US012804162B2

(12) United States Patent
Debnath et al.

(10) Patent No.: US 12,804,162 B2
(45) Date of Patent: Nov. 17, 2026

(54) ANALYTICS-AWARE VIDEO COMPRESSION CONTROL USING END-TO-END LEARNING

(71) Applicant: NEC Laboratories America, Inc., Princeton, NJ (US)

(72) Inventors: Biplob Debnath, Princeton, NJ (US); Deep Patel, Franklin Park, NJ (US); Srimat Chakradhar, Manalapan, NJ (US); Oliver Po, San Jose, CA (US); Christoph Reich, Hessen (DE)

(73) Assignee: NEC Corporation, Tokyo (JP)

( * ) Notice: Subject to any disclaimer, the term of this patent is extended or adjusted under 35 U.S.C. 154(b) by 99 days.

(21) Appl. No.: 18/439,291

(22) Filed: Feb. 12, 2024

(65) Prior Publication Data

US 2024/0275996 A1 Aug. 15, 2024

Related U.S. Application Data

(60) Provisional application No. 63/532,902, filed on Aug. 15, 2023, provisional application No. 63/488,810, (Continued)

(51) Int. Cl.
*H04N 19/146* (2014.01)
*A61B 34/00* (2016.01)
(Continued)

(52) U.S. Cl.
CPC ........... *H04N 19/146* (2014.11); *A61B 34/25* (2016.02); *B25J 9/1666* (2013.01); *G06N 20/00* (2019.01);
(Continued)

(58) Field of Classification Search
None
See application file for complete search history.

(56) References Cited

U.S. PATENT DOCUMENTS

2018/0261020 A1 9/2018 Petousis et al.
2018/0278895 A1 9/2018 Greenwood et al.
(Continued)

FOREIGN PATENT DOCUMENTS

EP 3975133 A1 3/2022
WO WO-2024031502 A1 * 2/2024 ........... H04L 5/0091

OTHER PUBLICATIONS

Zhang et al., "Understanding the Potential of Server-Driven Edge Video Analytics", Mar. 9, 2022, HotMobile '22: Proceedings of the 23rd Annual International Workshop on Mobile Computing Systems and Application, pp. 8-14 (Year: 2022).*
(Continued)

*Primary Examiner* — Kaitlin A Retallick
(74) *Attorney, Agent, or Firm* — Vincent Duffy

(57) ABSTRACT

Systems and methods are provided for optimizing video compression using end-to-end learning, including capturing, using an edge device, raw video frames from a video clip and determining maximum network bandwidth. Predicting, using a control network implemented on the edge device, optimal codec parameters, based on dynamic network conditions and content of the video clip, encoding, using a differentiable surrogate model of a video codec, the video clip using the predicted codec parameters and to propagate gradients from a server-side vision model to adjust the codec parameters. Decoding, using a server, the video clip and analyzing the video clip with a deep vision model located on the server, transmitting, using a feedback mechanism, analysis from the deep vision model back to the control network to facilitate end-to-end training of the system. Adjusting the encoding parameters based on the analysis from the deep vision model received from the feedback mechanism.

15 Claims, 13 Drawing Sheets

Related U.S. Application Data filed on Mar. 7, 2023, provisional application No. 63/445,046, filed on Feb. 13, 2023.

(51) Int. Cl.

| | |
|---|---|
| ***B25J 9/16*** | (2006.01) |
| ***G06N 20/00*** | (2019.01) |
| ***G06V 20/40*** | (2022.01) |
| ***G06V 20/58*** | (2022.01) |
| ***H04N 7/18*** | (2006.01) |
| ***H04N 19/119*** | (2014.01) |
| ***H04N 19/124*** | (2014.01) |
| ***H04N 19/14*** | (2014.01) |
| ***H04N 19/154*** | (2014.01) |
| ***H04N 19/156*** | (2014.01) |
| ***H04N 19/172*** | (2014.01) |
| ***H04N 19/176*** | (2014.01) |
| ***H04N 19/177*** | (2014.01) |
| ***H04N 19/42*** | (2014.01) |
| ***H04N 19/463*** | (2014.01) |
| ***H04N 19/61*** | (2014.01) |

(52) U.S. Cl.

CPC .............. *G06V 20/49* (2022.01); *G06V 20/58* (2022.01); *H04N 7/183* (2013.01); *H04N 19/119* (2014.11); *H04N 19/124* (2014.11); *H04N 19/14* (2014.11); *H04N 19/154* (2014.11); *H04N 19/156* (2014.11); *H04N 19/172* (2014.11); *H04N 19/176* (2014.11); *H04N 19/177* (2014.11); *H04N 19/42* (2014.11); *H04N 19/463* (2014.11); *H04N 19/61* (2014.11)

(56) References Cited

U.S. PATENT DOCUMENTS

| | | | | |
|---|---|---|---|---|
| 2019/0294869 | A1* | 9/2019 | Naphade ................ | G06V 20/54 |
| 2021/0208236 | A1 | 7/2021 | John Wilson et al. | |
| 2022/0375232 | A1 | 11/2022 | Furman et al. | |
| 2022/0385907 | A1* | 12/2022 | Zhang .................. | H04N 19/124 |

OTHER PUBLICATIONS

Said, Amir & Singh, Manish & Pourreza, Reza. (2023). Differentiable bit-rate estimation for neural-based video codec enhancement. 10.48550/arXiv.2301.09776. (Year: 2023).*

Du, K., Zhang, Q., Arapin, A., Wang, H., Xia, Z., & Jiang, J. (Apr. 26, 2022). Accmpeg: Optimizing video encoding for video analytics. arXiv preprint arXiv:2204.12534.

Liu, D., Li, Y., Lin, J., Li, H., & Wu, F. (Feb. 5, 2020). Deep learning-based video coding: A review and a case study. ACM Computing Surveys (CSUR), 53(1), 1-35.

Beye, F., Itsumi, H., Vitthal, C., & Nihei, K. (Oct. 16, 2022). Recognition-aware deep video compression for remote surveillance. In 2022 IEEE International Conference on Image Processing (ICIP) (pp. 1986-1990). IEEE.

* cited by examiner

400

800

900

ANALYTICS-AWARE VIDEO COMPRESSION CONTROL USING END-TO-END LEARNING

RELATED APPLICATION INFORMATION

This application claims priority to U.S. Provisional App. No. 63/445,046, filed on Feb. 13, 2023, and U.S. Provisional App. No. 63/488,810, filed on Mar. 7, 2023, and U.S. Provisional App. No. 63/532,902, filed on Aug. 15, 2023, each incorporated herein by reference in its entirety.

This application is related to U.S. patent application Ser. No. 18/439,341, now U.S. Pat. No. 12,542,909 entitled "ANALYTICS-AWARE VIDEO COMPRESSION FOR TELEOPERATED VEHICLE CONTROL", filed concurrently herewith, and which is incorporated by reference herein in its entirety.

BACKGROUND

Technical Field

The present invention relates to enhancements in video compression and analytics for network optimization and improved video analysis, and more particularly to an integrated system and method for adaptively controlling video compression based on deep learning techniques to achieve optimal balance between bandwidth efficiency and the analytical accuracy of video content in varying network conditions.

Description of the Related Art

In the realm of digital video processing and networked communication, significant advancements have been made to enhance video analytics and compression technologies. Traditional video encoding methods have often prioritized either bandwidth efficiency or analytical accuracy, facing challenges in dynamically adapting to fluctuating network conditions and analytical demands. Concurrently, video analytics systems have struggled with maintaining high accuracy in object detection and tracking due to variations in video quality, often caused by static compression settings that fail to account for changing scenes or environmental conditions. These limitations underscore the necessity for a more adaptive, intelligent approach to video compression and analytics, capable of optimizing both network bandwidth and the quality of video for analytics purposes. This backdrop highlights the evolving landscape of Internet of Things (IoT) applications, including surveillance, transportation, and healthcare, which demand innovative solutions to these longstanding issues.

Lossy compression is conventionally employed to cope with dynamic network-bandwidth conditions for streaming video data over a network. While more advanced video compression algorithms are available, the de facto standard is to utilize a unified video compression standard, such as H.264 or H.265. However, these video compression standards, trade compression strength (e.g., required bandwidth) against perceptual quality. Preserving the performance of a deep learning-based vision model is not conventionally considered, and thus, severe drops in performance are often the result when vision models analyze videos compressed by H.264.

SUMMARY

According to an aspect of the present invention, a system is provided for optimizing video compression using end-to-end learning, and includes one or more processor devices operatively coupled to a computer-readable storage medium. Raw video frames from a video clip are captured using an edge device, and maximum network bandwidth is determined. Optimal codec parameters are predicted, using a control network implemented on the edge device, based on dynamic network conditions and content of the video clip. The video clip is encoded using a differentiable surrogate model of a video codec using the predicted codec parameters and gradients are propagated from a server-side vision model to adjust the codec parameters. The video clip is decoded and analyzed with a deep vision model located on the server. Analysis from the deep vision model is transmitted, using a feedback mechanism, back to the control network to facilitate end-to-end training of the system, and the encoding parameters are adjusted based on the analysis from the deep vision model received from the feedback mechanism.

According to another aspect of the present invention, a method is provided for optimizing video compression using end-to-end learning, including capturing, using an edge device, raw video frames from a video clip and determining maximum network bandwidth. Predicting, using a control network implemented on the edge device, optimal codec parameters, based on dynamic network conditions and content of the video clip, encoding, using a differentiable surrogate model of a video codec, the video clip using the predicted codec parameters and to propagate gradients from a server-side vision model to adjust the codec parameters. Decoding, using a server, the video clip and analyzing the video clip with a deep vision model located on the server, transmitting, using a feedback mechanism, analysis from the deep vision model back to the control network to facilitate end-to-end training of the system. Adjusting the encoding parameters based on the analysis from the deep vision model received from the feedback mechanism.

According to another aspect of the present invention, a method is provided for optimizing video compression using end-to-end learning, including receiving a sequence of video frames and dividing said sequence into a plurality of groups, each group forming a Group of Pictures (GOP), transforming each video frame within each GOP into a series of image tokens, each token corresponding to a macroblock of the video frame, applying a Vision Transformer (ViT) model to said series of image tokens to encode spatial and temporal dependencies within and between video frames in the GOP, and utilizing a Multi-Head Attention (MHA) mechanism within the ViT model to process the image tokens by attending to each image token based on its relationship with other tokens within a same video frame and across different frames in the GOP and encoded video data. A file size of the encoded video is predicted, via a Multilayer Perceptron (MLP), from frame-wise file size tokens derived from the ViT model, where the frame-wise file size tokens are informed by positional embeddings that are extended to dimensionality of the GOP. The encoded video data is outputted with optimized encoding parameters determined by the ViT model applied to the sequence of image tokens.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION

Figure 1:
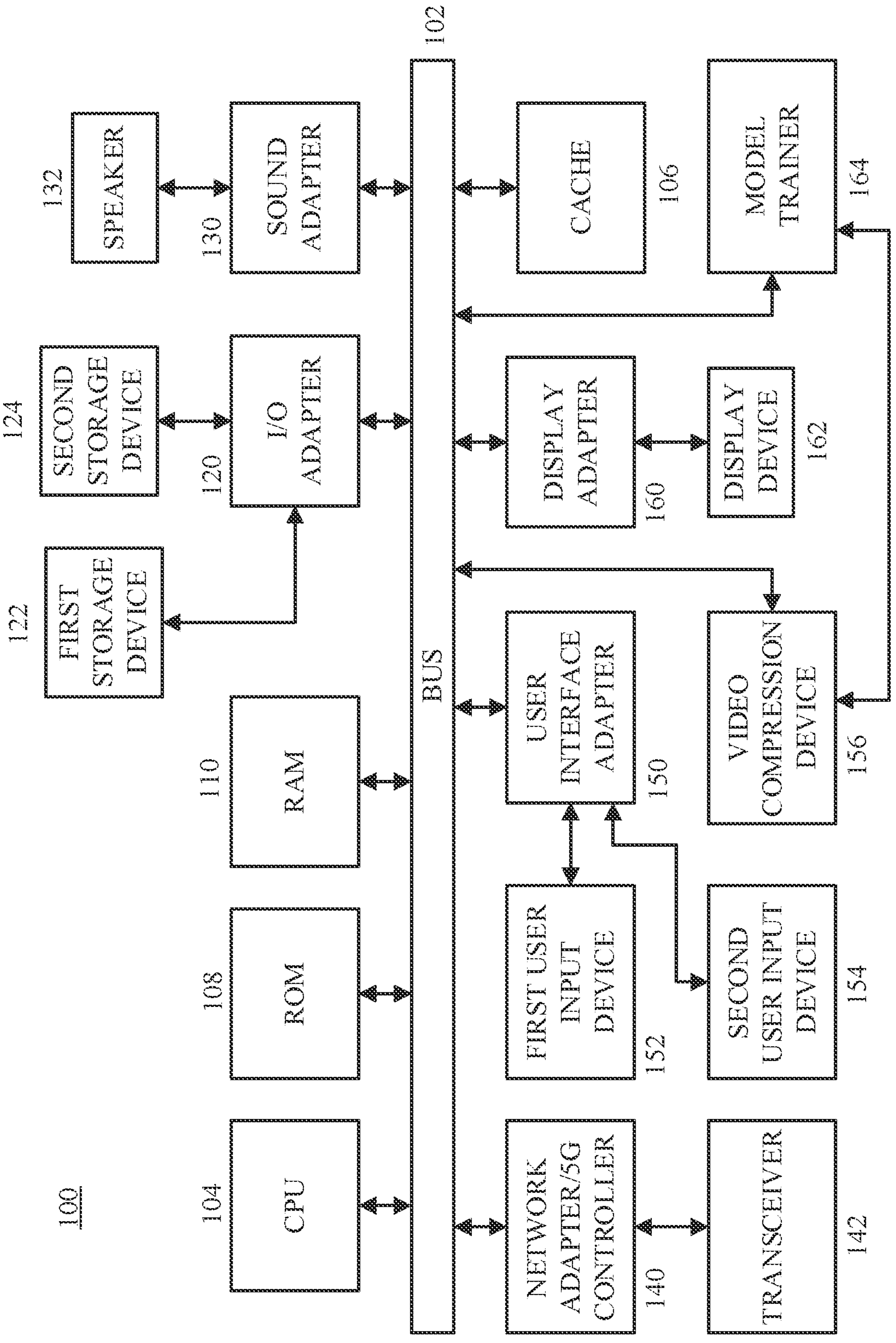
FIG. 1 is a block diagram illustratively depicting an exemplary processing system to which the present invention may be applied, in accordance with embodiments of the present invention.

In accordance with embodiments of the present invention, systems and methods are provided for enhancements in video compression and analytics for network optimization and improved video analysis. More particularly, the present invention can include an integrated system and method for adaptively controlling video compression based on deep learning techniques to optimize network bandwidth usage while maintaining high-quality video for analytics. The present invention can utilize surrogate model-based video encoding with reinforcement learning for dynamic adjustment of encoding parameters to achieve an optimal balance between bandwidth efficiency and the analytical accuracy of video content in varying network conditions.

In some embodiments, the present invention can control, for example, H.264 compression for preserving the performance of deep learning-based vision models. A differentiable surrogate model of a nondifferentiable H.264 codec can be employed to enable end-to-end learning with feedback from the server-side deep learning-based vision model, and task-agnostic end-to-end training for learning a lightweight control network can be utilized to manipulate the H.264 encoding. In some embodiments, the control network can learn to predict the optimal H.264 codec parameters for preserving the performance of a server-side vision model, while targeting a dynamic network-bandwidth condition.

Streamed video data is a major source of internet traffic. A significant and increasing amount of this video data is consumed and analyzed by deep learning-based vision models deployed on cloud servers. Streaming video data over a network with dynamic network conditions conventionally requires lossy video compression in order to meet network bandwidth constraints, but conventional deep learning-based vision models fail to provide adequate performance when analyzing lossy compressed videos in real-world streaming settings in practice.

The most common conventional approach for lossy video compression is to utilize a standardized video codec, such as H.264 or H.265. The H. 264 video codec was developed to find the best trade-off between compression and uniformly preserving the perceptual quality. However, this is not optimal for deep learning-based vision models, since they conventionally focus on particular salient parts of an image or video. Motivated by the performance gains and computing and processor resources savings, and that the H.264 is conventionally the de facto standard for video compression, the present invention can extend the H. 264 codec by predicting the optimal codec parameters for the current content and network-bandwidth condition, in accordance with aspects of the present invention.

In some embodiments, the present invention can control the H.264 codec (or any other codecs) by setting the optimal codec parameters to facilitate a content and network bandwidth aware dynamic compression, optimized for deep neural networks. In particular, a lightweight control network can be learned in an end-to-end setting to predict fine-grain codec parameters based on the current content and bandwidth constraint in order to preserve the performance of the server-side deep learning models, while targeting to meet the bandwidth constraint.

In various embodiments, the present invention does not include developing a new video codec for machines, but rather to control conventional codecs (e.g., the widely used H. 264 codec) for deep learning-based vision models as content and network bandwidth changes. Many already existing H.264-based implementations can be extended with a minor effort to utilize the control network of the present invention, rather than deploying a non-standardized video codec, which is conventionally not practical. Vision feature codecs often assume that the same feature extractor is employed, and thus, the server-side model needs to support the specific features. Additionally, just encoding and transferring vision features, drastically limits the option for human interventions, whereas the end-to-end learnable codec control of the present invention is not required to make any assumptions about the deep neural network utilized on the server-side.

In various embodiments, the encoding can be optimized for deep vision models, but it can still perform standard H.264 encoding and decoding on the video level, allowing for human interventions as desired. Conventional vision task-specific deep learning-based compression approaches offer strong compression results and can preserve the performance of a deep vision model, but similarly to other more general deep learning-based video compression approaches, task-specific deep learning-based compression approaches suffer from practical issues in real-world deployments, including the strong computational overhead and processor requirements induced by these approaches, and the very limited controllability with respect to the bandwidth. In various embodiments, H. 264 offers strong support for different compression strengths and can adapt to a wide range of bandwidths (typically multiple orders of magnitudes), H.264 encoding/decoding is computationally efficient, and our lightweight edge device side control network only adds a small amount of computational overhead, which increases processing speed and reduces required network resources, in accordance with aspects of the present invention.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid-state memory, magnetic tape, a removable computer diskette, a random-access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Aspects of the present invention are described below with reference to flowchart illustrations and/or block diagrams of methods, systems and computer program products according to embodiments of the present invention. It is noted that each block of the flowcharts and/or block diagrams, and combinations of blocks in the flowcharts and/or block diagrams, may be implemented by computer program instructions.

The flowchart and block diagrams in the figures illustrate the architecture, functionality, and operation of possible implementations of systems, methods and computer program products according to various embodiments of the present invention. Each block in the flowchart or block diagrams may represent a module, segment, or portion of code, which comprises one or more executable instructions for implementing the specified logical function(s), and in some alternative implementations of the present invention, the functions noted in the block may occur out of the order noted in the figures. For example, two blocks shown in succession may, in fact, be executed substantially concurrently, may sometimes be executed in reverse order, or may be executed in any other order, depending on the functionality of a particular embodiment.

It is also noted that each block of the block diagrams and/or flowchart illustration, and combinations of blocks in the block diagrams and/or flowchart illustration, can be implemented by specific purpose hardware systems that perform the specific functions/acts, or combinations of special purpose hardware and computer instructions according to the present principles.

Referring now to the drawings in which like numerals represent the same or similar elements and initially to FIG. 1, an exemplary processing system 100, to which the present principles may be applied, is illustratively depicted in accordance with embodiments of the present principles.

In some embodiments, the processing system 100 can include at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid-state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160. One or more video cameras 156 can be further coupled to system bus 102 by any appropriate connection system or method (e.g., Wi-Fi, wired, network adapter, etc.), in accordance with aspects of the present invention.

A first user input device 152 and a second user input device 154 are operatively coupled to system bus 102 by user interface adapter 150. The user input devices 152, 154 can be one or more of any of a keyboard, a mouse, a keypad, an image capture device, a motion sensing device, a microphone, a device incorporating the functionality of at least two of the preceding devices, and so forth. One or more video cameras 156 can be included, and the video cameras can include one or more storage devices, communication/networking devices (e.g., WiFi, 4G, 5G, Wired connectivity), hardware processors, etc., in accordance with aspects of the present invention. In various embodiments, other types of input devices can also be used, while maintaining the spirit of the present principles. The user input devices 152, 154 can be the same type of user input device or different types of user input devices. The user input devices 152, 154 are used to input and output information to and from system 100, in accordance with aspects of the present invention. A video compression device 156 can process received video input, and a model trainer 164 (e.g., neural network trainer) can be operatively connected to the system 100 for controlling video codec for deep learning analytics using end-to-end learning, in accordance with aspects of the present invention.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present principles provided herein.

Moreover, it is to be appreciated that systems 200, 300, 400, 500, 700, 800, 900, 1100, and 1300 described below with respect to FIGS. 2, 3, 4A, 4B, 5, 7, 8A, 8B, 9, 11, and 13, respectively, are systems for implementing respective embodiments of the present invention. Part or all of processing system 100 may be implemented in one or more of the elements of systems 200, 300, 400, 500, 700, 800, 900, 1100, and 1300 in accordance with aspects of the present invention.

Further, it is to be appreciated that processing system 100 may perform at least part of the methods described herein including, for example, at least part of methods 200, 300, 400, 500, 600, 700, 800, and 1000, described below with respect to FIGS. 2, 3, 4A, 4B, 5, 6, 7, 8A, 8B, 9, and 10, respectively. Similarly, part or all of systems 200, 300, 400, 500, 700, 800, 900, 1100, and 1300 may be used to perform at least part of methods 200, 300, 400, 500, 600, 700, 800, and 1000 of FIGS. 2, 3, 4A, 4B, 5, 6, 7, 8A, 8B, 9, and 10, respectively, in accordance with aspects of the present invention.

As employed herein, the term "hardware processor subsystem", "processor", or "hardware processor" can refer to a processor, memory, software, or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

Figure 2:
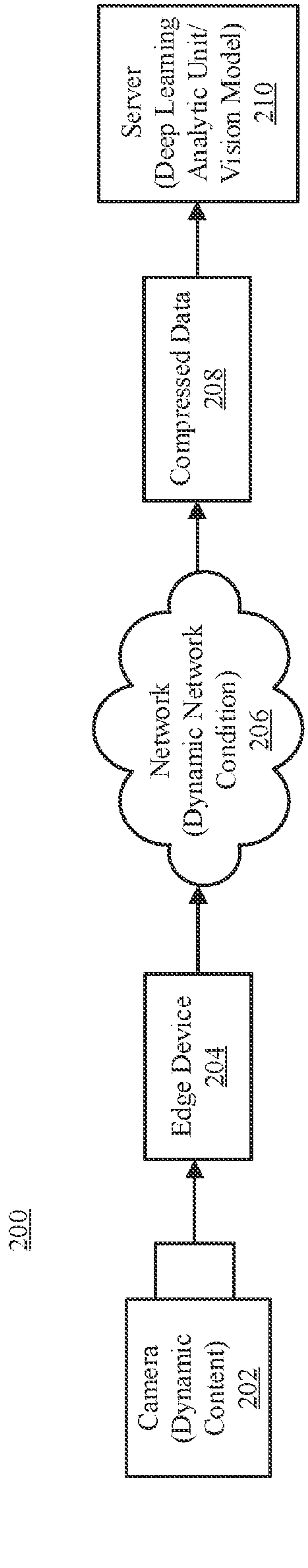
FIG. 2 is a diagram illustratively depicting a high-level view of a system and method for dynamic video compression and analysis for streaming video data over a network, in accordance with embodiments of the present invention.

Referring now to FIG. 2, a high-level view of a system and method 200 for dynamic video compression and analysis for streaming video data over a network, is illustratively depicted in accordance with embodiments of the present invention.

In an illustrative embodiment, a camera system 202 can be utilized to monitor an area of interest and/or capture live video and/or image data (e.g., dynamic content). The data can be transmitted to an edge device 204, which can serve as an initial processing point, including performing preliminary data compression, formatting, analysis, etc. before sending the video and/or image data to the network 206, which can include dynamic network conditions. In some embodiments, within the network 206, which represents various dynamic network conditions, the video data may be further compressed, shaped, or prioritized based on current bandwidth and latency metrics to ensure efficient transmission, in accordance with aspects of the present invention. This network 206 can dynamically adapt the data transmission based on real-time network traffic, bandwidth availability, and various other metrics, potentially altering the data's compression to suit the network conditions. The Compressed Data 208 represents the video data post network optimization, which is now streamlined for transmission efficiency and ready for analytical processing.

In some embodiments, the data next can be received by the Server (Deep Learning Analytic Unit/Vision Model) 210, where advanced video analytics can be performed. This server 210 can utilize deep learning models to analyze the video data for various applications, such as object detection, recognition, and tracking, and to extract meaningful insights from the compressed video data, in accordance with aspects of the present invention. Each block in FIG. 2 represents important steps in the process of capturing, transmitting, and analyzing video data in real-time, ensuring that the dynamic content captured by the camera 202 is efficiently processed and analyzed despite the constraints and variability of network conditions.

While the single camera system 202 is shown in FIG. 2 for the sakes of illustration and brevity, it is to be appreciated that multiple camera systems can also be used, in accordance with aspects of the present invention.

In an illustrative embodiment, based on the general video streaming setting shown in FIG. 2, a codec control can be formulated as a constrained planning problem as follows:

$$\max_{(codec\ parameters)} \text{Analytics Model Performance} \quad (1)$$

$$\text{s.t. Bitrate} \leq \text{Target Bandwidth}$$

For example, a target bandwidth constraint of $10^5$ bits per second can be satisfied by range of codec parameter values (e.g., Quantization Parameter (QP) values from at least 20 to 30) and Equation (1) can select a codec parameter value that results in the maximum possible accuracy of the analytics model, given the target bandwidth constraint. In some embodiments, H. 264 encoding parameters for preserving the performance of a server-side deep vision model while matching a current network-bandwidth requirement can be predicted, and in practice, multiple parameter configurations can satisfy Equation (1).

In some embodiments, given a short video clip and the currently available network bandwidth, the present invention can estimate the codec parameters such that the resulting video stream does not exceed the available network bandwidth. Additionally, when analyzing the encoded/decoded clip with a deep-learning vision model, the performance can be maintained as compared to the performance on the raw clip. Formally, three control requirements to be met by our H. 264 control can be defined: (i) maintain the performance of the server-side deep learning-based vision model, (ii) do not exceed the available bandwidth, preventing information from being dropped by the network, and (iii) perform the codec parameter prediction and encoding in a single forward pass, avoiding complicated feedback loops or multipass encoding, in accordance with aspects of the present invention.

In various embodiments, the present invention can include an end-to-end learnable control of the H. 264 video compression standard for deep learning-based vision models. The present invention can include utilizing a differentiable surrogate model of the non-differentiable H. 264 video codec, which enables differentiating through the video encoding and decoding. In particular, we can propagate gradients from the server-side deep learning vision model through the codec to learn our codec control. Further, a task-agnostic end-to-end training formulation for learning a lightweight edge device side control network to control the H.264 for deep vision models can be implemented utilizing the surrogate model. By utilizing a differentiable surrogate model of the non-differentiable H. 264 codec, we ensure a full differentiability of pipeline. This allows us to utilize end-to-end self-supervised learning, circumventing the use of reinforcement learning, in accordance with aspects of the present invention.

Conventional systems and methods utilize the feedback of a cloud server to decide how a video should be compressed for the server-side deep network. However, a feedback loop leads to a complicated architecture, requires additional bandwidth for the feedback, and adds an additional point of failure, limiting the applicability of such approaches. These approaches also assume that the server-side network runs only a specific task (e.g. object detection). In avoidance of such drawbacks, the present invention can utilize a feedback loop-free and server-side task agnostic codec control pipeline, in accordance with various aspects of the present invention.

Figure 3:
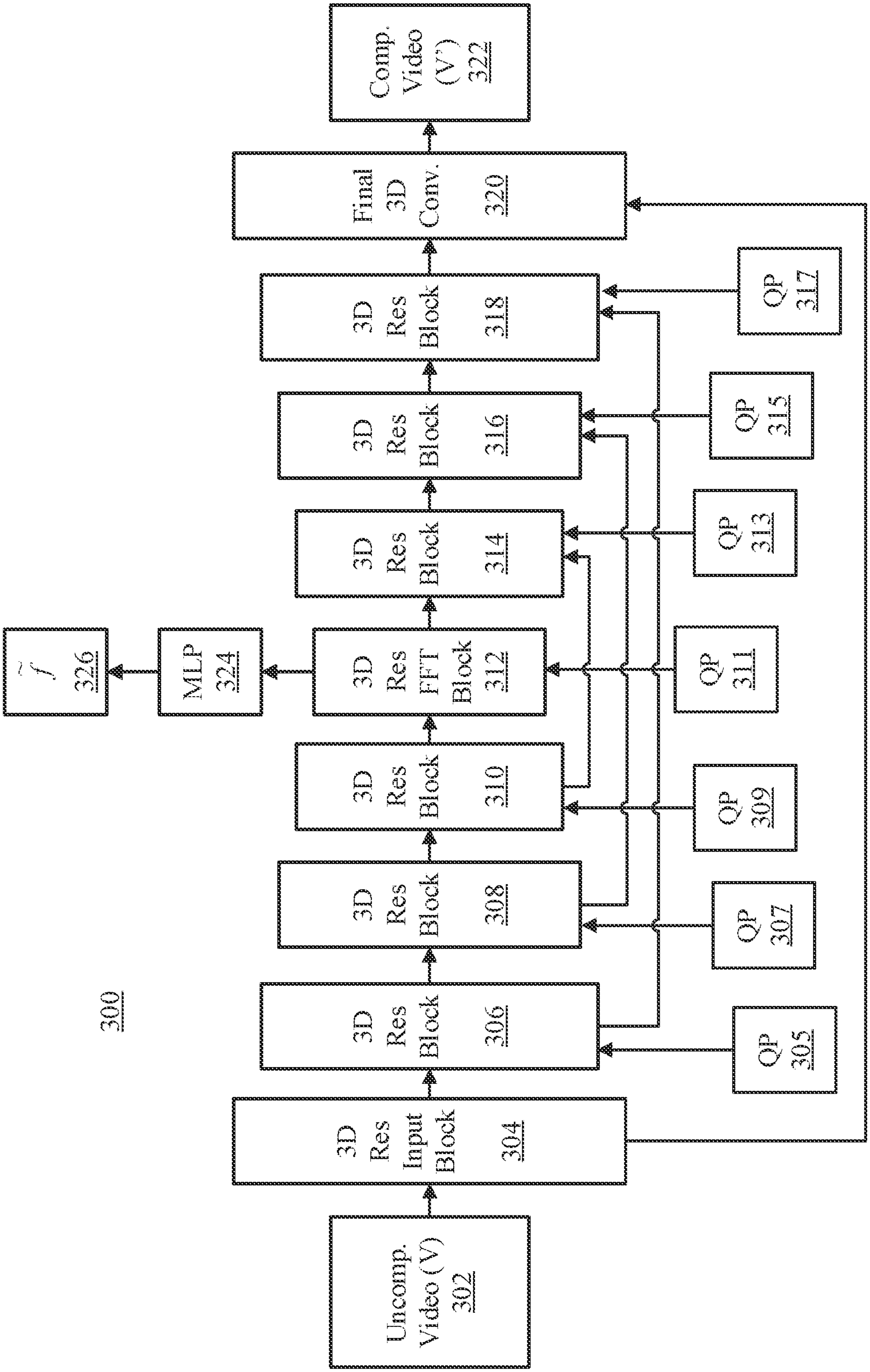
FIG. 3 is a diagram illustratively depicting an adaptive video compression system and method including a surrogate model architecture for optimizing video encoding parameters in real-time using machine learning, in accordance with embodiments of the present invention.

Referring now to FIG. 3, a diagram showing an adaptive video compression system and method 300 including a surrogate model architecture for optimizing video encoding parameters in real-time using machine learning, is illustratively depicted in accordance with embodiments of the present invention.

In accordance with embodiments of the present invention, note that H.264/AVC performs efficient video compression by making use of image compression techniques and temporal redundancies. The predictive coding architecture of the H. 264 codec utilizes sophisticated hand-crafted transformations in order to analyze redundancy within videos. A macroblock-wise motion-compensated discrete cosine transform followed by a quantization step can be used to perform compression. In the standard setting, H. 264 performs lossy compression but also supports lossless compression. In practice, H. 264 is conventionally employed as a lossy compression algorithm to aggressively compress videos.

The H. 264 codec allows for a variety of different customizations to the compression process. A crucial codec parameter for controlling the compression strength and video quality is the quantization parameter (QP), controlling how strong the transformation coefficients are quantized. QP ranges from 0 to 51 (integer range), with high values leading to stronger compression. While strong compression leads to reduced file sizes/bandwidth, this is at the cost of perceptual quality. For a given set of codec parameters, the file size/bandwidth remains dependent on the video content in a non-trivial manner.

The group of pictures (GOP) size also influences the resulting compression, by controlling which frames should be encoded as an I, B, or P-frame. I-frames (intra-coded frames) are only compressed by utilizing spatial redundancies (similar to image compression), whereas B-frames (bidirectional predicted frames) and P-frames (predicted frames) are compressed by also using information from adjacent frames. In particular, B-frames are compressed by utilizing a previous and a subsequent I- or P-frame. For compressing P-frames only a single previous I- or P-frame is used. I-frames typically require more bits than B and I frames. The quantization parameters (QP) highly influence the performance of current action recognition models. For example, when employing a QP value of 51, the accuracy of all models drops from above 70% (no compression) to below 50%. In particular, the R(2+1)D–50 model achieves an accuracy of 74.01% with no H. 264 employed but using full compression (QP=51), the accuracy drops down to 34.67%, halving the performance. Generally, a similar behavior is observed for other H.264 parameters (e.g., constant rate factor and GOP) and demonstrated training on compressed videos also entails a performance drop.

H. 264 offers support for macroblock-wise quantization, in which regions of the video, in this exemplary case, 16×16 frame patches (macroblocks), are compressed with varying QP values. Thus, irrelevant regions can be compressed with a high QP value (strong compression) and relevant regions with a lower QP value (less compression). In various embodiments, macroblock-wise quantization can be employed to facilitate a fine-grain spatial and temporal control of the compression strength, in accordance with aspects of the present invention.

Macroblock-wise quantization offers several major advantages over standard region-of-interest approaches. While region-of-interest-based approaches detect a single and small region of interest, macroblock-wise quantization can express multiple interesting regions. The ability to express multiple regions of interest enables macroblock-wise quantization to adapt to complex scenes without inducing ambiguities, maintaining the analytics performance. Fully discarding unimportant regions, as conventionally done by region-of-interest-based approaches, limits the applicability to other vision tasks. Macroblock-wise quantization does not fully discard unimportant regions but performs aggressive compression on these regions. The resulting data can still be utilized for other vision tasks, such as object detection, in accordance with aspects of the present invention.

Supporting only a single region of interest (e.g., conventionally done by region-of-interest-based approaches) can induce ambiguities, subsequently deteriorating the analytic performance of complex action recognition tasks. For illustration, consider the example of a child is walking a dog. In order to correctly classify the present action (e.g., walking the dog), an action recognition model needs to be informed of the child, the dog leash, and the dog. Otherwise, ambiguities are introduced and the action recognition model might predict the action walking or running. Similarly, with respect to an example of a person playing basketball, without being informed of the basketball hoop, it is not clear if the person is just throwing a ball or if the person is playing basketball.

In various embodiments, macroblock-wise quantization overcomes these limitations by offering support for multiple regions of interest and retaining the context of the entire frame. In general, macroblock-wise compression can be intuitively interpreted as a soft generalization of region-of-interest approaches with support for multiple regions of interest in a single frame. This flexibility and generalization enables a wide application of our codec control pipeline to different vision tasks, such as action recognition, object detection, or instance segmentation, in accordance with aspects of the present invention.

Formally, we consider the macroblock-wise H. 264 codec as a function mapping from the original video V and QP parameters QP to both the encoded and decoded video $\hat{V}$ and the file size f of the encoded video:

$$H.264(V, QP) = (\hat{V}, f),\ f \in \mathbb{R}^{+} \qquad (2)$$

$$V, \hat{V} \in \{0, \ldots, 255\}^{3\times T\times H\times W},$$

$$QP \in \{0, \ldots, 51\}^{T\times H/16\times W/16}.$$

Where T indicates the video length and H×W the spatial dimensions of the RGB video. Other H. 264 parameters are considered to be constant.

In practice, this H. 264 function (Equation (2)) is not differentiable with respect to the QP parameters (compression strength). To overcome this limitation, the present invention can utilize a differentiable surrogate model for the H. 264 codec. This surrogate model enables us to train a control network with gradient information from both the server side model and the generated bandwidth. Intuitively, this surrogate model fulfills two tasks during training. Firstly, it allows the control network to explore and learn which regions are important for the server side model prediction based on gradient information, and secondly, the control network can learn the non-trivial relationship between the codec parameters (QP) and the file size (required bandwidth) of the compressed video, in accordance with aspects of the present invention.

In various embodiments, the architecture illustrating an adaptive video compression system and method 300 (e.g., H.264 surrogate model architecture) for optimizing video encoding parameters in real time using machine learning, can be based on a 3D residual U-Net with Conditional Group Normalization (CGN). In block 302, uncompressed video (V) can be fed into a 3D Residual Input Block 304. This block is designed to process the initial video frames, preparing them for subsequent layers by extracting initial feature representations. The system can include multiple 3D Residual Blocks 306, 308, 310, 316, and 318, each receiving Quantization Parameters (QP) 305, 307, 309, 313, 315, and 317, respectively, which can adjust the level of compression applied at each stage, in accordance with aspects of the present invention.

In some embodiments, a 3D Residual Fast Fourier Transform (FFT) Block 312 is incorporated to transform spatial domain data into the frequency domain, enhancing the model's ability to handle various frequency components within the video data efficiently. The QP 311 associated with this block allows for selective frequency compression, which can be crucial for preserving important information while reducing file size. The Multi-Layer Perceptron (MLP) 324 can be utilized to predict the final file size 326 ($\tilde{f}$) of the compressed video. This prediction is used to adjust the QPs dynamically, ensuring the compressed video does not exceed bandwidth limitations while maintaining quality, in accordance with aspects of the present invention.

The final stage involves a Final 3D Convolution Block 320 that consolidates the processed data into a format suitable for reconstruction, leading to the output of the compressed video (V') 322. Each block in the system can be interconnected, with QPs feeding into each, indicating a sophisticated control mechanism over the compression process. This system architecture demonstrates an advanced approach to real-time adaptive video compression, leveraging deep learning to maintain video quality in the face of bandwidth constraints and network variability, in accordance with aspects of the present invention.

The U-Net's encoder-decoder structure takes in the uncompressed video V and predicts the approximated compressed video V. Each encoder and decoder block is conditioned on the given QP parameters by utilizing Conditional Group Normalization (CGN). Based on the average pooled features of the bottleneck block, a multilayer perceptron (MLP) predicts the approximated file size $\tilde{f}$ of the encoded video. Note that the surrogate model 300 uses one-hot encoded QP parameters, denoted as $qp \in [0,1]^{51\times T\times H/16\times W/16}$. This design choice allows for later formulating the prediction of the integer-valued QP parameters by the control network as a classification problem, in accordance with aspects of the present invention.

Figure 4B:
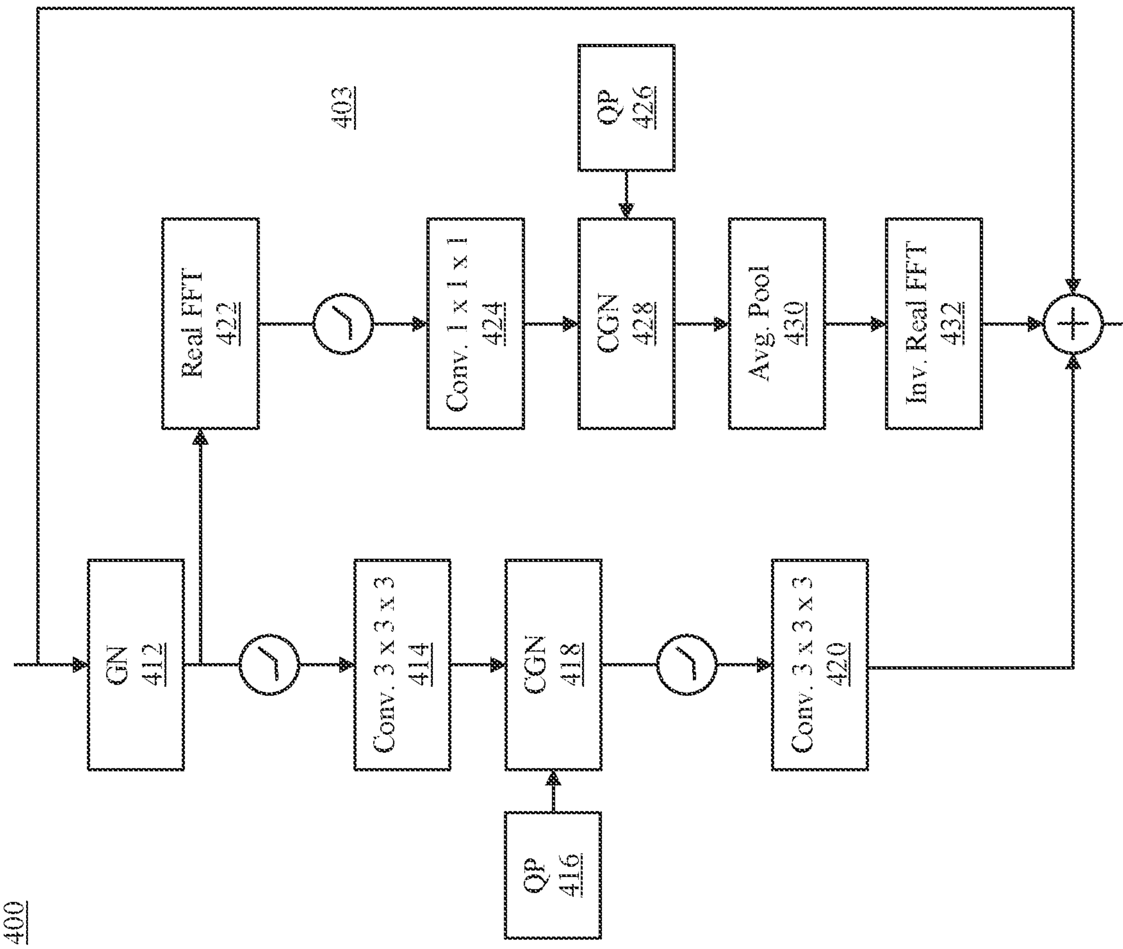
FIG. 4B is a diagram illustratively depicting a system and method for video processing using a surrogate model block configuration including a 3D residual Fast Fourier Transform (FFT) block, in accordance with embodiments of the present invention.
Figure 4A:
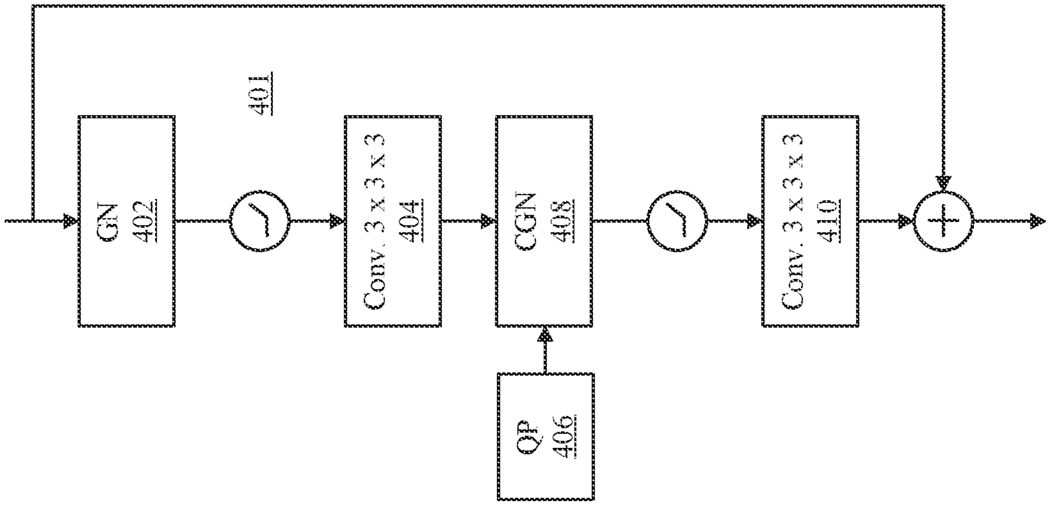
FIG. 4A is a diagram illustratively depicting a system and method for video processing using a surrogate model block configuration including a 3D residual block, in accordance with embodiments of the present invention.

Referring now to FIG. 4A, a diagram showing a system and method 400 for video processing using a surrogate model block configuration including a 3D residual block 401, is illustratively depicted in accordance with embodiments of the present invention.

In some embodiments, a 3D residual block architecture 401 for video processing can include a Group Normalization (GN) layer 402, which can normalize the features within a group of channels to stabilize the learning process. This can be followed by a convolutional layer 404 with a kernel size of 3×3×3, denoted by the symbol with a diagonal line, which indicates that this layer performs spatial-temporal convolution on the input features. The Quantization Parameters (QP) 406 are fed into a Conditional Group Normalization (CGN) layer 408, suggesting that this layer adjusts its normalization based on the QP, which can modulate compression to balance video quality and size. Another convolutional layer 410, also with a kernel size of 3×3×3, processes the normalized features. The output of this convolutional layer is then combined with the output of a previous layer or input feature map through the plus sign in the circle, which symbolizes an element-wise addition, indicative of a residual learning connection within the block. Each block and connection within FIG. 4A represents a step in processing video data, enhancing the model's ability to extract features and compress video data effectively while being conditioned by the quantization parameters for optimal encoding, in accordance with aspects of the present invention This configuration within FIG. 4A can enable the neural network model to learn and adapt to various data features and conditions, which can be particularly advantageous in video processing applications that require dynamic adjustment to compression and quality parameters.

In various embodiments, a core building block of the surrogate model is a 3D residual block. The 3D residual block first performs standard Group Normalization (GN), before the normalized features are fed into a Gaussian Error Linear Unit (GELU) activation. The resulting features are fed into a 3×3×3 convolution. Next, CGN can be used to incorporate the QP parameters. A GELU can be utilized as a non-linearity before a 3×3×3 convolution is employed. Finally, a residual addition can be performed. Encoder blocks can employ a spatial stride of two in the second convolution for spatial downsampling. The decoder can utilize trilinear interpolation to upsample the spatial dimensions again before every block. The skip connection can utilize a 1×1×1 convolution and an optimal stride to match the output feature size. The 3D residual input block can utilize an augmented version of the 3D residual block, omitting the first GN and GELU, and additionally, CGN can be replaced with GN, in accordance with aspects of the present invention.

Referring now to FIG. 4B, a diagram showing a system and method 400 for video processing using a surrogate model block configuration including a 3D residual Fast Fourier Transform (FFT) block 403, is illustratively depicted in accordance with embodiments of the present invention.

In various embodiments, a 3D residual FFT bottleneck block 403 can be initiated with a Group Normalization (GN) layer 412, which can normalize the input data across a set of channels. Following the GN layer, a convolutional layer 414 with a kernel size of 3×3×3 can perform spatial-temporal feature extraction. Quantization Parameters (QP) 416 can be input into a Conditional Group Normalization (CGN) layer 418, which can conditionally adjust the normalization process according to the QP. Subsequently, another convolutional layer 420 with a kernel size of 3×3×3 can further process the features. On a parallel branch, a Real Fast Fourier Transform (FFT) layer 422 can transform the feature set into the frequency domain, which is then processed by a smaller convolutional layer 424 with a kernel size of 1×1×1. A second CGN layer 428, also receiving QP 426, can normalize these features.

In some embodiments, an Average Pooling layer 430 can reduce the spatial dimensions of the feature set, followed by an Inverse Real FFT layer 432, which can transform the features back into the spatial domain. The outputs of both branches can then be merged using an element-wise addition, as indicated by the plus sign, forming the output of the 3D residual FFT bottleneck block 403, in accordance with aspects of the present invention.

In some embodiments, inspired by H.264, which utilizes the discrete cosine transform as part of the compression procedure, the present invention can utilize a 3D residual FFT block in the bottleneck stage of the U-Net. This block can introduce inductive biases related to the original H. 264 compression. The standard 3D residual block can be extended by a Fourier branch. This branch can perform a real FFT 422 on the normalized feature maps before employing a GELU activation, a 1×1×1 convolution 424, a CGN layer 428, and an average pooling layer 430 to the features in frequency space. Finally, an inverse real FFT is used to transform the features back into the spatio-temporal domain. The resulting features can be added to the output features.

In order to encode the information of the QP parameters into our surrogate model architecture, Conditional Group Normalization can be utilized. Similar to Conditional Batch normalization can be performed without fixed affine parameters. We predict the affine transformation, after normalization, based on the input QP parameters. Formally, the Conditional Group Normalization layer can be defined as:

$$\hat{X} = MLP_{\mu}(qp) \cdot GroupNorm(X) + MLP_{\sigma}(qp)$$

where X is a 4 D spatio-temporal input feature map and X is the output feature map of the same shape. GroupNorm donates the standard Group Normalization operation without affine parameters, applied to the channel dimension, over a pre-defined number of groups. Two point-wise multilayer perceptrons ($MLP_{\mu}$ & $MLP_{\sigma}$) can predict the affine transformation based on the one-hot qp parameters. In practice, MLP can be implemented as two 1×1×1 convolutions with GELU activation. To ensure matching spatial dimensions between the feature map and transformation, nearest neighbor interpolation can be employed to the output of $MLP_{\mu}$ and $MLP_{\sigma}$.

In various embodiments, the surrogate model can approximate both the H. 264 function (Equation (2)) and its derivative. Based on the control variates theory, the surrogate model can become a low-variance gradient estimator of Equation (2) if the difference between the output of the surrogate model and the true H. 264 function is minimized, and the two output distributions are maximizing the correlation coefficients ρ. We can enforce both requirements for $\tilde{V}$ and $\tilde{f}$ by minimizing:

$$\mathcal{L}_s = \mathcal{L}_{s_v} + \mathcal{L}_{s_f}$$

during training. Where $\mathcal{L}_{s_v}$ is computed with the approximated compressed video $\tilde{V}$, whereas, $\mathcal{L}_{s_f}$ is computed based on the predicted file size $\tilde{f}$. As the video surrogate loss $\mathcal{L}_{s_v}$, we utilize $$\mathcal{L}_{s_v} = -\alpha_{\rho_v}\mathcal{L}_{\rho_v} + \alpha_{SSIM}\mathcal{L}_{SSIM} + \alpha_{FF}\mathcal{L}_{FF}$$

where $\mathcal{L}_{\rho_v}$, is the correlation coefficient loss ensuring the correlation coefficient ρ is maximized. $\mathcal{L}_{SSIM}$ is the structural similarity (SSIM) loss and $\mathcal{L}_{FF}$ donates the focal frequency loss.

In some embodiments, both the SSIM loss and the focal frequency loss are employed to ensure that the difference between $\hat{V}$ and $\tilde{V}$ is minimized. We motivate the use of the focal frequency loss $\mathcal{L}_{FF}$ by the discrete cosine transform-based compression of the H. 264 codec. Since H. 264 performs macroblock-wise quantization, we can also apply the focal frequency loss $\mathcal{L}_{FF}$ on a per-macroblock level. As the file size surrogate loss $\mathcal{L}_{s_f}$, we can use:

$$\mathcal{L}_{s_f} = -\alpha_{\rho_f}\mathcal{L}_{\rho_f} + \alpha_{L1}\mathcal{L}_{L1}$$

where $\mathcal{L}_{\rho f}$ is the correlation coefficient loss between the true file size f and the predicted file size $\tilde{f}$. For minimizing the difference between f and $\tilde{f}$ an L1 loss $\mathcal{L}_{L1}$ is used. Note that we learn the file size in $\log_{10}$ space, due to the large range of file sizes, and $\alpha_{\rho_v}$, $\alpha_{SSIM}$, $\alpha_{FF}$, $\alpha_{\rho f}$, and $\alpha_{L1}$ denote the respective positive weight factors, in accordance with aspects of the present invention.

Figure 5:
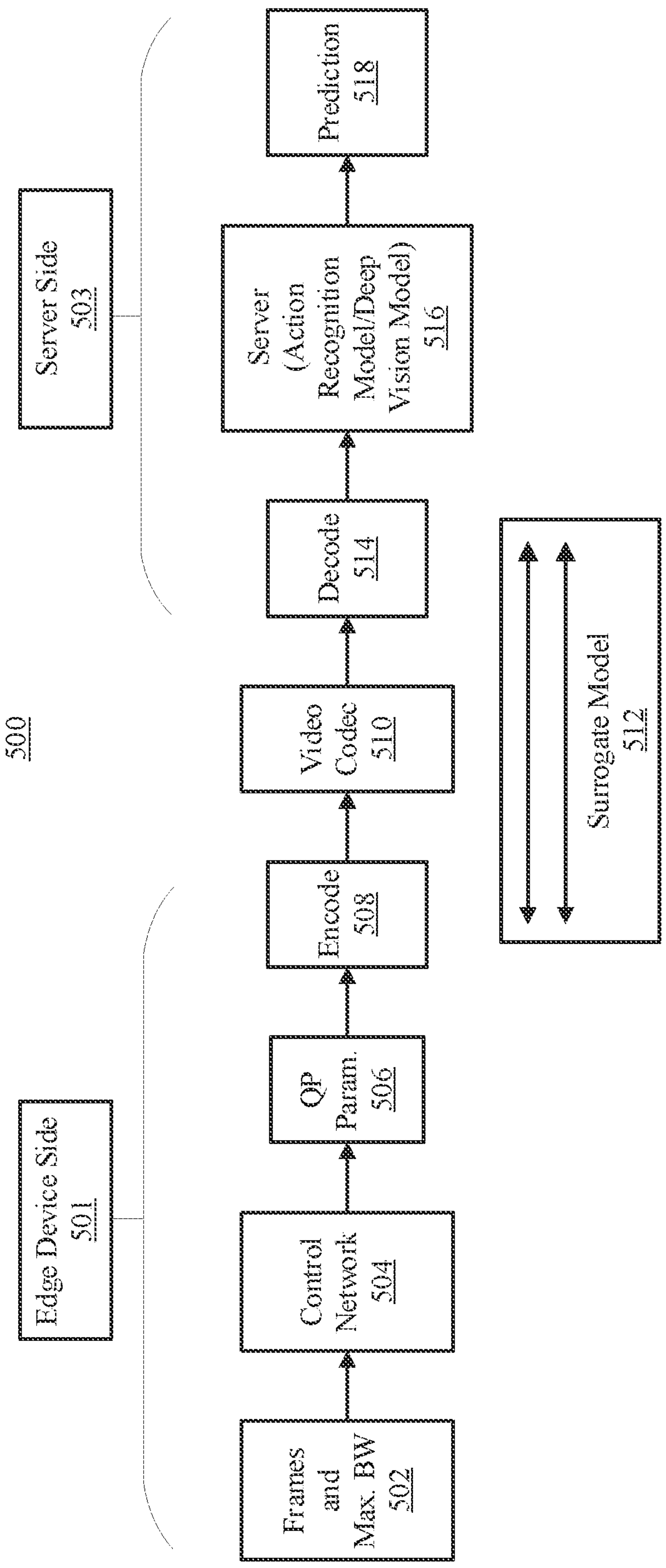
FIG. 5 is a diagram illustratively depicting a system and method for end-to-end codec control for video compression systems, in accordance with embodiments of the present invention.

Referring now to FIG. 5, a diagram showing a system and method 500 for end-to-end codec control for video compression systems is illustratively depicted in accordance with embodiments of the present invention.

In various embodiments, an Edge Device Side 501 can initiate the process with the edge device components. This segment can include the functionalities of capturing frames, bandwidth determination, and initial codec parameter prediction processes, which can be critical for adapting the video stream to the dynamic conditions of the network and the requirements of the edge device. The server side 503 represents the server-side operations that receive the encoded video stream. The server side is responsible for decoding the video and conducting deep learning analyses, such as action recognition, through the server's deep vision model. The outcome of this process is the prediction output, which is the analytical result based on the compressed video content after considering the optimal compression parameters to maintain performance fidelity despite the compression process.

In some embodiments, in block 502, frames along with the maximum bandwidth parameter can be introduced as the initial inputs to the system. These frames are the dynamic video content intended for analysis, and the maximum bandwidth parameter dictates the allowable data rate for video streaming. The control network, represented by block 504, predicts optimal Quantization Parameters (QP) that are conducive to maintaining the balance between video compression efficiency and the analytic performance of deep learning models, in accordance with the content and network bandwidth constraints.

In some embodiments, block 506 is responsible for the application of the predicted QP to the frames, which is then followed by the encoding process in block 508. This process involves compressing the video using the H.264 codec, ensuring that the encoded video stream is within the boundaries set by the available network bandwidth while also retaining the necessary quality for subsequent analysis. The video codec, noted as block 510, can then facilitate the transition from the encoding process to decoding in block 514, where the video is reverted to a format suitable for analysis by the server-side model.

In various embodiments, block 512 illustrates the surrogate model, which is a differentiable representation of the H.264 codec, allowing for backpropagation of gradients from the server-side model through the codec during the learning phase. This model can be pivotal for refining the control network's predictive capabilities, in accordance with aspects of the present invention. In block 516, the server on the server-side model 503, which may include an action recognition model or a deep vision model, analyzes the decoded video. The performance of this analysis is benchmarked against the uncompressed video to ascertain that the compression has not detrimentally impacted the analytic outcomes. The final output of the system is shown in block 518, which is the prediction result produced by the server-side model after analyzing the video content. This output can be used for various purposes, such as activity recognition or other deep learning tasks, in accordance with aspects of the present invention.

In various embodiments control of the H. 264 codec can be learned by training a control network 504 to predict the optimal QP parameters for the current content and available bandwidth. We learn the control network 504 by utilizing a simple end-to-end training formulation, facilitated by the H. 264 surrogate model. Note that while we demonstrate our general training pipeline on action recognition in this paper, the pipeline is agnostic to the type of task performed by the server side model.

The control network 504 can predict the optimal QP-parameters, to be employed by the H. 264 codec, given a short video/clip and the current maximum available bandwidth. To facilitate an easy real-world deployment, the present invention can utilize a very lightweight control network. For example, it can utilize X3D-S (or similar) as the backbone of our control network 504. In order to ensure the correct spatial shape of the output, the striding in the last stage of the X3D-S network can be omitted in some embodiments. To encode the bandwidth condition into the network's prediction, we can omit the classification head of the X3D-S model and utilize two residual blocks with CGN (e.g., FIG. 4A) as the prediction head.

The prediction of the integer-valued QP parameters can be formalized as a classification problem. In particular, the control network can learn to predict a logit vector over the different QP values for each macroblock. During training, the Gumbel-Softmax trick can be used to produce a differentiable one-hot vector based on the predicted logits. During inference, the arg max can be used to generate the one-hot vector over QP values. When used as an input to the H. 264 codec (Equation (2)) and not to the surrogate model, the arg max function can be applied to the one-hot prediction, in accordance with aspects of the present invention.

In some embodiments, the control network 504 can be trained in an end-to-end setting on the control requirements. By utilizing the H. 264 surrogate model, the bandwidth can be directly minimized until the dynamic bandwidth requirement is met. Our control network 504 takes also direct feedback from the server side model 516 by propagating gradients from the output of the server side model 516 through the video codec surrogate model to the control network. Formally, the control network 504 can be trained to minimize:

$$\mathcal{L}_c = \alpha_p \mathcal{L}_p + \alpha_b \mathcal{L}_b$$

This control network loss $\mathcal{L}_c$ is composed of a performance loss $\mathcal{L}_p$ and a bandwidth loss $\mathcal{L}_b$, $\alpha_p$ and $\alpha_b$ are the respective positive loss weight factors. The performance loss is used to ensure that the performance of the server side model is maintained. In the case of action recognition, we employ the Kullback-Leibler divergence $$\sum_{i=1}^{c} y_i \log \frac{y_i}{\tilde{y}_i}$$

between the action recognition prediction of the compressed video $\tilde{y} \in \mathbb{R}^c$ and the prediction of the uncompressed video $y \in \mathbb{R}^c$. We also refer to y as the pseudo label. Note that using a different server side model 516 (e.g. an object detection model) can involve adapting the performance loss $\mathcal{L}_p$ to the new task.

In various embodiments, the bandwidth loss $\mathcal{L}_b$ ensures that the bandwidth required to transfer the video is minimized until the bandwidth condition is met. Formally, minimize $\mathcal{L}_B = \max(0, \tilde{b} - b(1-\epsilon))$, where b is the maximum available bandwidth (bandwidth condition). $\tilde{b}$ denotes the estimated bandwidth based on the surrogate model's file size prediction $\tilde{f}$. We convert the file size (in bytes) to the bandwidth (in bit/s), with known frame rate (fps), number of video frames T, and the temporal stride $$\Delta t, \text{ by } \tilde{b} = \frac{8\tilde{f}ps}{T\Delta t}.$$

We use a small $\epsilon$ in order to enforce the generated bandwidth to be smaller than the available bandwidth.

In some embodiments, both the control network 504 and the surrogate model 512 can be trained in an alternating fashion. However, in order to ensure a stable training of the control network from the beginning, the surrogate model 516 can be pre-trained before fine-tuning it in the control network training. The control network's training is depicted in pseudocode in Algorithm 1, below:

Algorithm 1 Pseudocode of our end-to-end control training in a PyTorch-like style.

```
for video, bw_max in data_loader;
  # Forward pass control network
  qp_one_hot = control_network (video, bw_max)

  # Forward pass of surrogate model
  video_s, fs_s = h264_surrogate (video, qp_one_hot)

  Prediction on transcoded video
  pred = act_rec_model (video_s)

  # Generate pseudo label with uncompressed video
   with no_grad ( ):
      label_pseudo = act_rec_model (video)

  # Convert file sizes to bandwidths
  Bw_s = file_size_to_bandwidth (fs_s)

  # Compute loss (Eq. (7))
  loss = alpha_b * loss_b (bw_s, bw_max) \
     + alpha_p * loss_p (pred, label_pseudo)

```

-continued

Algorithm 1 Pseudocode of our end-to-end control training in a PyTorch-like style.

```
  # Compute backward pass and perform optimization
  loss.backward ( )
  optimizer_control_network.step ( )
  # Next: Make surrogate model training step
```

In various embodiments, two metrics can be utilized to validate the codec control. The bandwidth condition accuracy ($acc_b$) measures how well our control meets the bandwidth condition. The performance accuracy ($acc_p$), computed between the arg max of the pseudo label y and the codec control prediction $\tilde{y}$ for a given bandwidth condition. Note for simplicity we do not consider frame dropping or other realworld behavior of a dynamic network when exceeding the bandwidth limit while computing $acc_p$. Following common practice, we can compute both the top-1 and top-5 performance accuracy, noting that the H. 264 codec itself is used for validation, and not the surrogate model, in accordance with aspects of the present invention.

Figure 6:
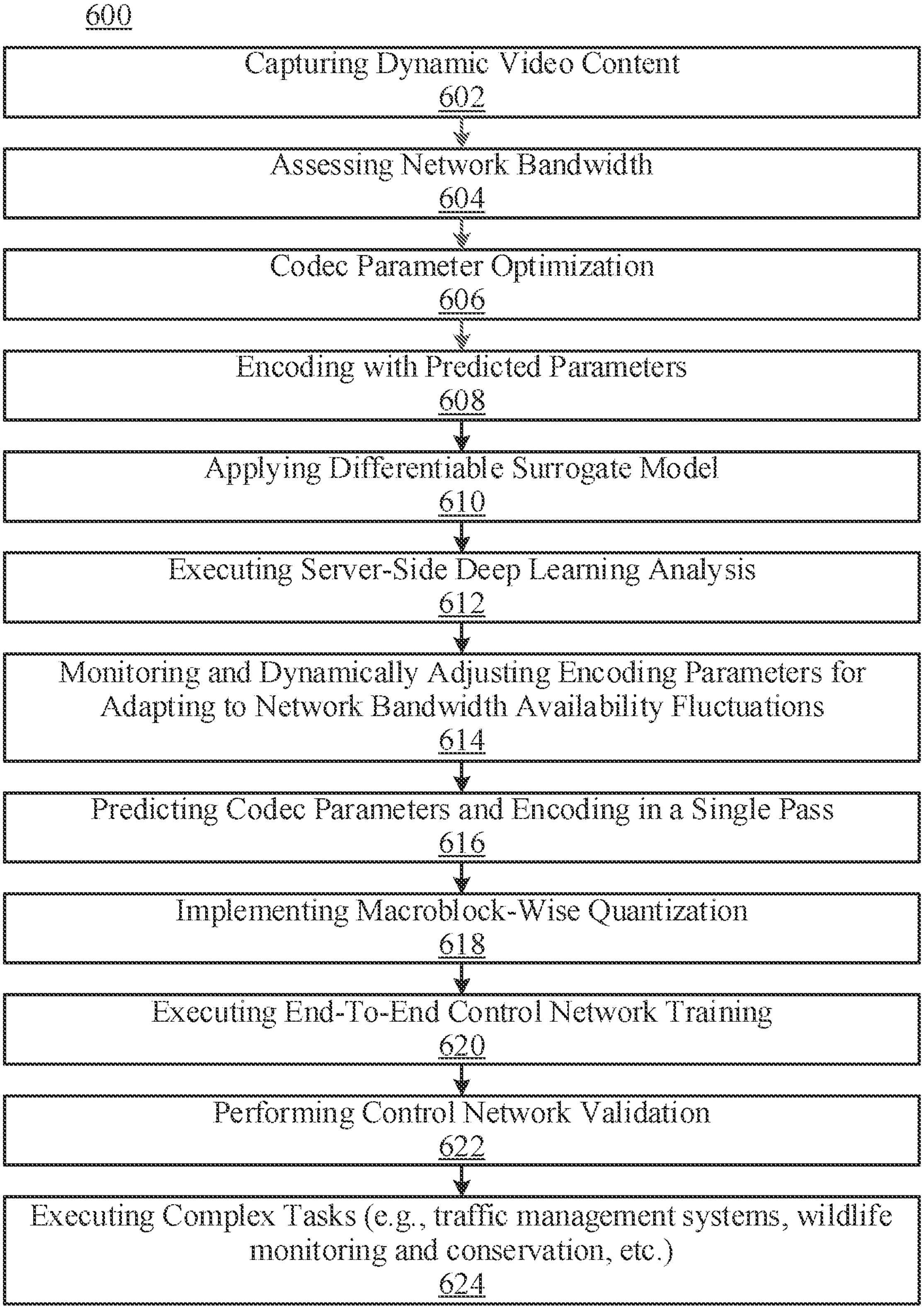
FIG. 6 is a block/flow diagram illustratively depicting a method for optimizing end-to-end video compression control using deep learning models under varying network conditions, in accordance with embodiments of the present invention.

Referring now to FIG. 6, a block/flow diagram showing a method 600 for optimizing end-to-end video compression control using deep learning models under varying network conditions, is illustratively depicted in accordance with embodiments of the present invention.

In some embodiments, in block 602, dynamic video content capture can be performed by utilizing a camera system to capture dynamic video content. The process is intricately designed to cater to the nuanced requirements of downstream deep learning models. The captured content, rich in detail and variety, is set to undergo a series of sophisticated compression algorithms aimed at preserving the integrity and analytic utility of the video data. The content's intrinsic characteristics such as motion vectors, frame rate, resolution, and color depth are meticulously preserved to maintain high fidelity to the original scene. In block 604, network bandwidth assessment can include a thorough assessment of the prevailing network conditions, particularly the available bandwidth for video data transmission. This step is critical for the adaptive compression algorithm, which tailors the video stream's bitrate to the fluctuating network capacity. The assessment entails real-time monitoring and prediction algorithms that consider historical data trends, current network traffic, and predictive analytics to set a dynamic target bandwidth threshold. This threshold serves as a pivotal reference for the compression parameter adjustments that follow.

In block 606, codec parameter optimization can be performed using a control network, leveraging advanced machine learning techniques, to undertake the task of predicting the most optimal set of H.264 codec parameters. These parameters are meticulously chosen to strike an equilibrium between the twin objectives of minimizing bandwidth consumption and maximizing the performance of deep learning-based video analytics models. The control network employs complex optimization algorithms, considering the content's characteristics and the assessed network bandwidth, to predict quantization parameters that will yield an encoded video stream of the highest analytical value.

In block 608, encoding with predicted parameters can be executed. In this phase, the video content is encoded using the H.264 codec, which now operates with the fine-tuned quantization parameters prescribed by the control network. This step ensures that the video stream is compressed in such a manner that it does not surpass the network bandwidth limitations. The encoding process is a sophisticated blend of temporal and spatial compression techniques, including intra-frame and inter-frame predictions, transform coding, and entropy encoding, all adjusted to work within the parameters set to ensure optimal bandwidth utilization without sacrificing video quality.

In block 610, a differentiable surrogate model of the H.264 codec is deployed, which enables a differentiable pathway through the video encoding and decoding processes. This model is integral to the training and refinement of the control network, as it allows for the backpropagation of gradients from the server-side analytics model. The surrogate model is a novel construct that mirrors the codec's functionality while allowing for the mathematical differentiation that standard codecs do not support. This surrogate model can represent a pivotal innovation that links video compression to analytical performance in an unprecedented manner, in accordance with aspects of the present invention.

In block 612, server-side deep learning analysis can be performed by subjecting the compressed video to a comprehensive analysis by a server-side deep learning vision model. This model, which is benchmarked against uncompressed video to validate the compression's impact, utilizes convolutional neural networks, recurrent neural networks, or other suitable architectures to extract actionable insights from the video data. The analysis focuses on a range of attributes from object detection and classification to more complex tasks such as behavior prediction and anomaly detection, ensuring that the compression process retains sufficient quality for these advanced analytical operations.

In block 614, encoding parameters for adapting to network bandwidth availability fluctuations can be monitored and dynamically adjusted. In block 614, bandwidth constraint compliance can ensure rigorous compliance with the set bandwidth constraints during video streaming. This can be achieved through real-time monitoring systems that dynamically adjust encoding parameters to adapt to any fluctuations in network bandwidth availability. The objective is to transmit every bit of information without loss, preventing the dropping of critical data that could impact the analytics model's performance.

In block 616, codec parameter prediction and encoding can be executing in a single forward pass, avoiding the traditional complexities associated with feedback loops or multi-pass encoding strategies. This innovation streamlines the compression pipeline, significantly reducing latency, and computational overhead, thereby facilitating a more efficient and agile encoding process suitable for real-time applications. In block 618, macroblock-wise Quantization can be implemented. This is a technique that allows for differential compression across various regions of each video frame. The quantization process is content-aware, assigning varying levels of compression based on the importance of each macroblock to the overall video analytics goals. This nuanced approach ensures that critical regions of the frame are preserved with higher fidelity, while less important areas are compressed more aggressively to save bandwidth, in accordance with aspects of the present invention.

In block 620, end-to-end control network training can be executed, and the control network can be trained from the ground up, leveraging the capabilities of the differentiable surrogate model. This training is designed to directly align with the overarching goals of the system, which include maintaining the performance of maintaining server-side model performance and ensuring efficient utilization of available bandwidth. The training involves simulating various network conditions and content types to create a robust model capable of handling real-world streaming scenarios.

In block 622, control network validation can be performed, and can include conducting a rigorous validation process on the control network, utilizing metrics designed to measure the network's adherence to bandwidth conditions and the maintenance of deep learning model performance. This validation ensures the network's predictions are not only theoretically sound but also practically effective in managing bandwidth without compromising the analytical utility of the video content. In block 624, complex tasks (e.g., traffic management, wildlife monitoring and conservation, etc.) can be executed by applying the codec control method, demonstrating the control network's versatility and adaptability. This application signifies the method's efficacy in not only traditional video analytics scenarios but also in dynamic and latency-sensitive environments, where maintaining high-quality video streams within strict bandwidth constraints is paramount, in accordance with aspects of the present invention.

Figure 7:
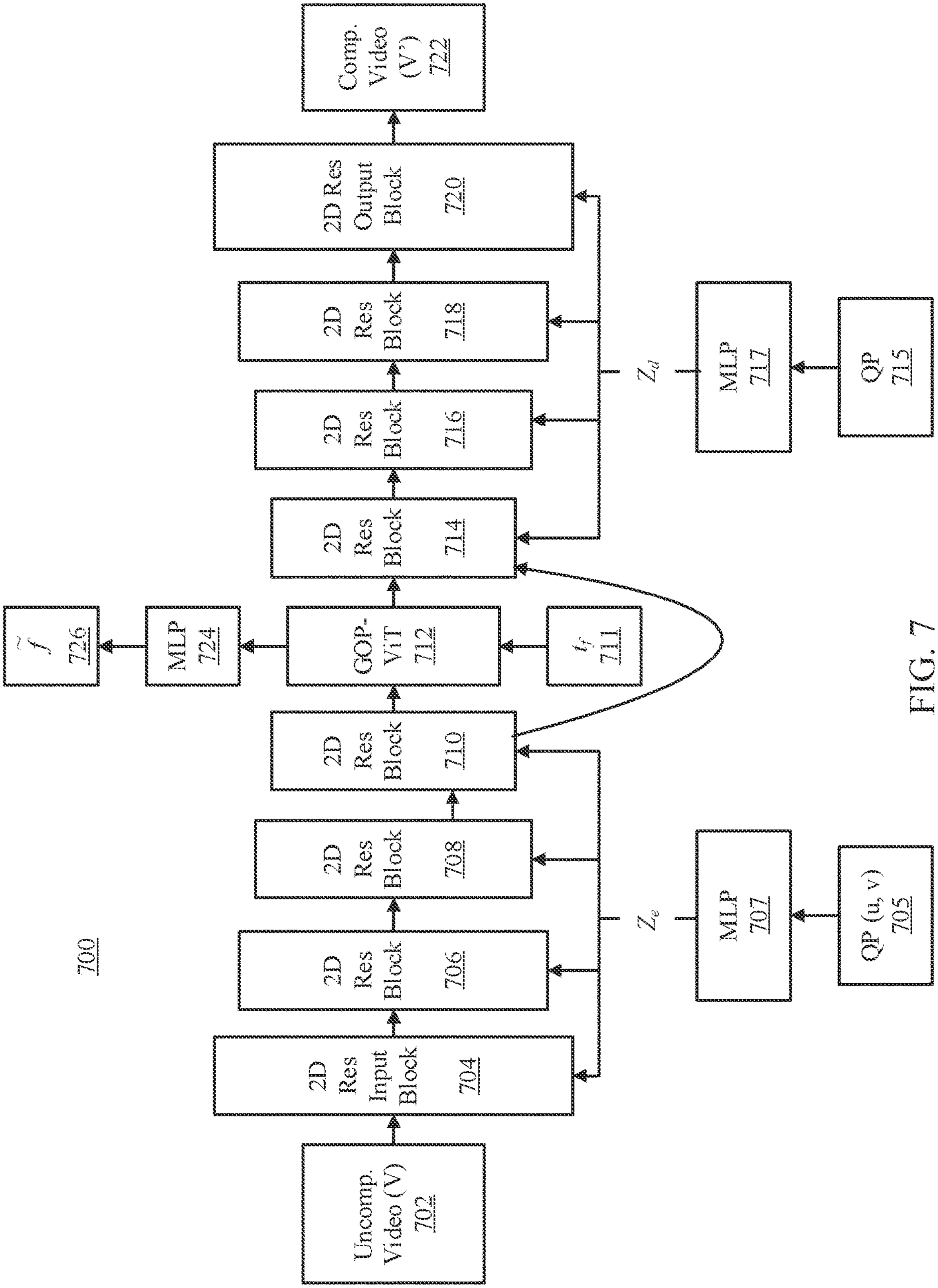
FIG. 7 is a diagram illustratively depicting an adaptive video compression system and method including a surrogate model architecture for optimizing video encoding parameters in real-time using machine learning, in accordance with embodiments of the present invention.

Referring now to FIG. 7, a diagram showing an adaptive video compression system and method 700, including a surrogate model architecture for optimizing video encoding parameters in real-time using machine learning, is illustratively depicted in accordance with embodiments of the present invention. In various embodiments, the architecture can effectively learn and control macroblock-wise quantization parameters (QP) for video compression, enabling a differentiable approximation of the H.264 codec, thus facilitating end-to-end learning for video distortion versus file size trade-off control.

In some embodiments, the model can take uncompressed video (V) 702 as input and processes it through a series of 2D Residual (Res) Blocks 704, 706, 708, and 710. These blocks are designed for encoding video frames into feature embeddings at the frame level, capturing spatial dependencies. Each 2D Res Block is a convolutional unit that applies learned filters to the input, contributing to the surrogate model's ability to approximate the original video V. At the heart of the architecture lies the GOP-ViT block 712, which can be crucial for learning both spatial and temporal dependencies. It predicts the file size f as well as feature embeddings for the decoder. The GOP-ViT block is conditioned on the file size token $t_f$ 711 and utilizes a differentiable attention mechanism to model temporal relations within the group of pictures (GOP).

In various embodiments, the decoder section of the architecture is symmetrical to the encoder, with 2D Res Blocks 714, 716, 718, and 720, which utilize the feature embeddings from the GOP-ViT block to reconstruct the compressed video prediction V' 722. The symmetrical design ensures that the model can effectively learn the inverse mapping from compressed feature embeddings back to video frames. Conditioning on macroblock-wise QP parameters can be achieved through two separate Multilayer Perceptrons (MLPs) 707 and 717, which embed the QP parameters for the encoder and decoder, respectively. These MLPs allow for fine-grained control over the compression parameters at the macroblock level. The use of one-hot encoded QP parameters facilitates the prediction of integer-valued QP as a classification problem, enabling precise control over compression levels across different regions of the video frame.

In various embodiments, the surrogate model architecture 700 can integrate two distinct conditional embeddings $Z_e$ and $Z_d$, which can be utilized for conditioning the encoder and decoder parts of the model, respectively. The encoder conditioning $Z_e$ plays an important role in the encoding process by providing additional contextual information that could influence how the video frames are encoded into feature embeddings. This contextual information can include details derived from the macroblock-wise quantization parameters and may also incorporate motion vectors or other relevant data that can guide the encoder in prioritizing certain areas of the video frame over others, based on their importance for the reconstructed video quality.

On the other side, the decoder conditioning $Z_d$ can be utilized during the decoding process to ensure that the decoder is aware of the encoding context, allowing for a more accurate reconstruction of the compressed video V' 722 from the feature embeddings. By providing the decoder with this conditional information, the model can better understand how to interpret the compressed features, which is essential for minimizing the loss of information during the video compression process. In practice, $Z_e$ and $Z_d$ can serve as bridges between the encoder and decoder, ensuring that both components of the model are synchronized in terms of their objectives and the compression parameters being applied. This can lead to a more efficient and effective video compression model that can dynamically adjust to the content of the video frames and the desired compression outcomes, in accordance with aspects of the present invention.

In some embodiments, the macroblock-wise flow vectors (u, v) 705 can be used to condition the encoder, making the surrogate model optical flow-aware. This allows the model to take into account motion within the video when encoding and compressing frames, an important aspect of effective video compression. An MLP 724 can be used to regress the file size of the encoded video from the frame-wise file size token, ensuring that the model can predict not only the visual quality of the compressed video but also its file size, an important factor in bandwidth management. The file size MLP 726 in the architecture 700 serves as the final processing step for predicting the file size $\tilde{f}$ of the encoded video. After the GOP-ViT block 712 outputs the intermediate file size token $t_f$ 711, this token is further processed by the file size MLP 724, which captures the complex relationship between the compressed feature embeddings and the resultant file size.

In some embodiments, the file size MLP 726 averages over the number of frames T and applies additional transformation to accurately regress the final predicted file size $\tilde{f}$. This step is important for optimizing the trade-off between video quality and file size, and for making informed decisions about the compression strength at a macroblock level throughout the video sequence, in accordance with aspects of the present invention.

In various embodiments, the surrogate model architecture 700 can combine reversible GOP-ViT with conditional encoding and decoding, all within a differentiable framework that supports macroblock-wise quantization. This enables the control network to learn the complex relationship between video quality, file size, and compression parameters, thereby achieving efficient and intelligent video compression, in accordance with aspects of the present invention.

Figure 8B:
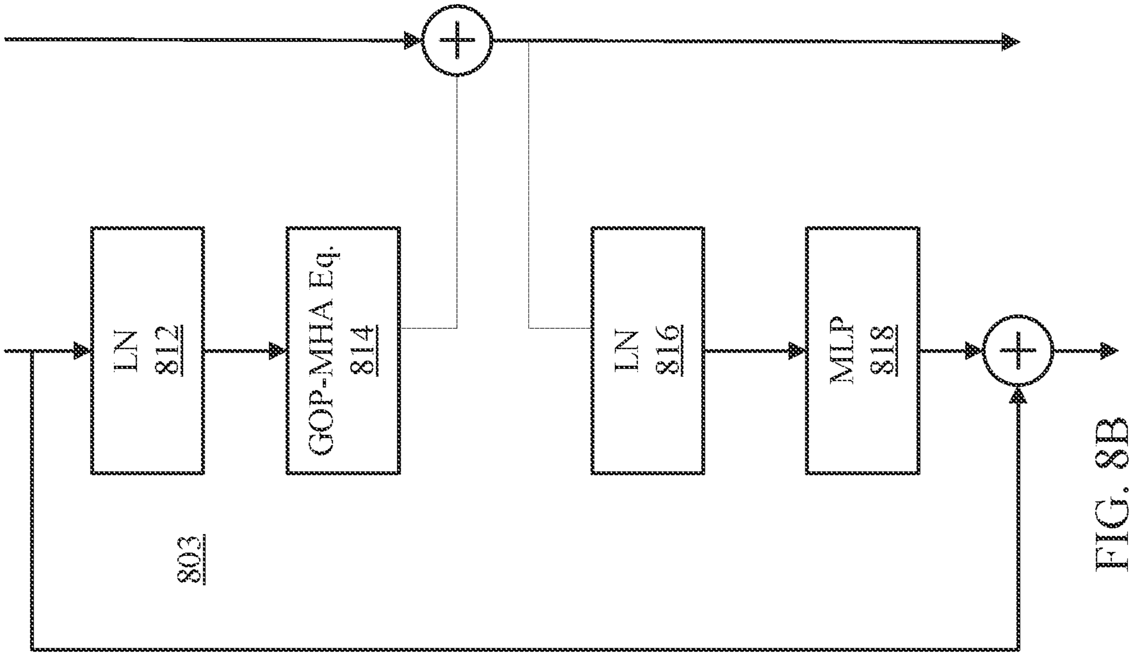
FIG. 8B is a diagram illustratively depicting a system and method for video processing using a surrogate model block configuration including a Group of Pictures—Vision Transformer (GOP-ViT) block, in accordance with embodiments of the present invention.
Figure 8A:
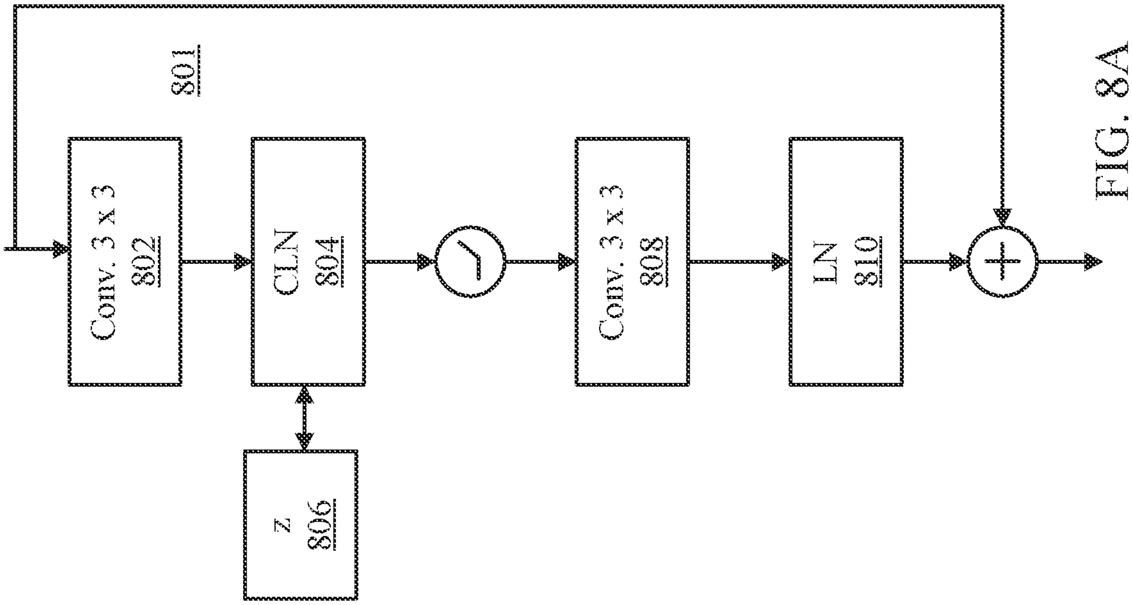
FIG. 8A is a diagram illustratively depicting a system and method for video processing using a surrogate model block configuration including a 2D residual block, in accordance with aspects of the present invention.

Referring now to FIG. 8A, a diagram showing a system and method 800 for video processing using a surrogate model block configuration, including a neural network architecture utilizing 2D residual block 801 for video compression, is illustratively depicted in accordance with embodiments of the present invention. The neural network architecture including 2D residual blocks 801 is designed to process video data using a series of layers and operations to facilitate efficient video compression while preserving the quality of the video.

In some embodiments, the architecture 801 includes a first convolutional layer 802, which applies a 3×3 convolutional operation to the input data. This layer is responsible for detecting low-level features from the input and creating feature maps for further processing. Following the first convolutional layer 802, a Conditional Layer Normalization (CLN) layer 804 is applied. The CLN layer incorporates a conditional embedding z 806, which allows the layer to adjust its normalization parameters based on the condition provided, thus enabling the model to be aware of additional contextual information such as video content or compression parameters. The architecture then includes a subtraction operation, where the output of the CLN layer 804 is subtracted from a bypass connection that directly carries the input data from before the first convolutional layer 802. This bypass connection allows the architecture to form a residual block, which helps in training deeper networks by allowing gradients to flow through the network more effectively.

In various embodiments, a second convolutional layer 808 is utilized, performing another 3×3 convolutional operation. This layer further processes the feature maps, building upon the low-level features extracted by the first convolutional layer 802. A Layer Normalization (LN) layer 810 can be utilized next, and unlike the CLN layer 804, the LN layer can apply a standard normalization operation without conditional embeddings, which standardizes the output of the neural network, making training more stable and efficient, in accordance with aspects of the present invention.

Referring now to FIG. 8B, a diagram showing a system and method 800 for video processing using a surrogate model block configuration, Group of Pictures—Vision Transformer (GOP-ViT) block 803, is illustratively depicted in accordance with embodiments of the present invention. The GOP-ViT block 803 is an important component of a video compression architecture designed to efficiently process video clips by learning both spatial and temporal dependencies. This GOP-ViT block 803 is composed of two Layer Normalization (LN) layers 812 and 816, which normalize the features within a layer by subtracting the mean and dividing by the standard deviation. LN layers are important for stabilizing the learning process and allowing for higher learning rates. An MLP (Multilayer Perceptron) 818, follows the LN layers, which is a type of feedforward neural network that consists of at least three layers of nodes: an input layer, a hidden layer, and an output layer. MLPs can capture a wide range of nonlinear relationships within the data, in accordance with aspects of the present invention.

In some embodiments, both the encoder and the decoder can be comprised of 2D residual blocks, and striding can be utilized in the second convolution to downsample the spatial resolution of the feature maps in the encoder. Decoder blocks can omit the striding and the first convolution can be replaced with a transposed convolution to upsample the spatial resolution of the feature maps by a factor of two, and can utilize Layer Normalization and Gaussian Error Linear Units (GELU). The encoder and decoder can be conditioned on the condition embeddings $z_e$ and $z_d$, respectively, and for the conditioning, a Conditional Layer Normalization (CLN) layer can be utilized in each encoder and decoder block. CLN can be composed of a standard Layer Normalization without affine parameters followed by a Spatial Feature Transform for incorporating the conditioning, in accordance with aspects of the present invention.

In various embodiments, the GOP-MHA (Group of Pictures-Multi-Head Attention) layer 814, can be a variant of the multi-head attention mechanism that allows the model to jointly attend to information from different representation subspaces at different positions. In the context of video compression, this layer can help the model to understand and compress the temporal relationships within a group of pictures (GOP). Inspired by the H.264 codec, the GOP-ViT employs a structure that compresses videos within a GOP and is designed to reduce computational and memory complexity compared to traditional methods that would process a large sequence of tokens. The GOP-ViT block operates on a sequence of image tokens $T_1, T_2, \ldots, T_m$ with a fixed length T, representing the GOP. Each image embedding $T_i$ is made up of n tokens with an embedding dimension d, which corresponds to the number of macroblocks in each frame predicted by the encoder.

Block 816 represents a Layer Normalization (LN) layer which is a technique to stabilize the learning process in neural networks. It normalizes the input layer by re-centering and re-scaling, which can lead to faster training and reduced sensitivity to network initialization. Block 818 represents a Multilayer Perceptron (MLP), which is a class of feedforward artificial neural network. MLPs consist of at least three layers of nodes: an input layer, a hidden layer, and an output layer. In various embodiments, the MLP 818 can be used to process the normalized features from the LN layer to perform tasks such as regressing the file size of the encoded video or making predictions about the video content based on learned features.

In some embodiments, this architecture is particularly optimized for video clips structured in the well-known GOP format, such as [IBBBPBBP] for a GOP of 8, facilitating efficient processing by attending each frame with itself and all corresponding frames based on the GOP structure. The described GOP-MHA layer can be formally represented as follows:

$$\hat{T}_{i,I} = MHA(T_{i,I}, T_{i,I}, T_{i,I})$$

$$\hat{T}_{i,P} = MHA\big(T_{i,P}, \big(T_{i,P}, T_{-1,P/I}\big), \big(T_{i,P}, T_{1,P/I}\big)\big)$$

$$\hat{T}_{i,B} = MHA\big(T_{i,B}, \big(T_{i,B}, T_{-1,P/I}, T_{+1,P/I}\big)$$

$$\big(T_{i,B}, T_{-1,P/I}, T_{+1,P/I}\big)\big)$$

where the second subscript denotes the frame type. $T_{-1,P/I}$ indicates the nearest previous P-frame or I-frame, whereas $T_{+1,P/I}$ indicates the nearest subsequent one. $(\cdot,\cdot)$ denotes a concatenation along the token dimension. MHA represents the standard Multi-Head-Attention operation. We can stack multiple GOP-ViT blocks together to form a GOP-ViT in the bottleneck of our surrogate model, in accordance with aspects of the present invention.

In some embodiments, the present invention can employ standard learnable positional embeddings, extended to the GOP dimension, with the input features. Inspired by the classification token used in the ViT, we can utilize a frame-wise file size token $t_f \in \mathbb{R}^{m \times 1 \times d}$ which can be concatenated to the sequence of image tokens. After the GOP-ViT we can extract the frame-wise file size token, average over the number of frames T, and utilize an MLP to regress the file size of the encoded video. To further reduce the memory footprint of our GOP-ViT, the reversible ResNet structure can be applied to our GOP-ViT block, in accordance with aspects of the present invention.

In various embodiments, the surrogate model can approximate both the H. 264 function (Equation (2)) and its derivative. Based on the control variates theory, the surrogate model can become a low-variance gradient estimator of Equation (2) if the difference between the output of the surrogate model and the true H. 264 function is minimized and the two output distributions are maximizing the correlation coefficients ρ. The present invention can enforce both requirements for $\tilde{V}$ and $\tilde{f}$ by minimizing $\mathcal{L}_s = \mathcal{L}_{s_v} + \mathcal{L}_{s_f}$ during training, where $\mathcal{L}_{S_v}$ is computed with the predicted compressed video $\tilde{V}$, and $\mathcal{L}_{s_f}$ is computed based on the predicted file size $\tilde{f}$. As the video surrogate loss $\mathcal{L}_{s_v}$, we can utilize $\mathcal{L}_{S_f} = -\alpha_{\rho_v}\mathcal{L}_{\rho_v} + \alpha_{SSIM}\mathcal{L}_{SSIM} + \alpha_{FF}\mathcal{L}_{FF} + \alpha_1\mathcal{L}_l$, where $\mathcal{L}_{\rho_v}$ is the correlation coefficient loss ensuring the correlation coefficient ρ is maximized. $\mathcal{L}_{SSIM}$ is the structural similarity (SSIM) loss and $\mathcal{L}_{FF}$ denotes the focal frequency loss. $\mathcal{L}_1$ is a latent space loss.

In some embodiments, during surrogate model pre-training, we can use the VGG loss at layer RELU3_3, and when fine-tuning the surrogate model during the codec control training, we can use output prediction of the server-side model for computing $\mathcal{L}$ 1. The SSIM loss, the focal frequency loss, and the latent space loss can be employed to ensure that the difference between $\hat{V}$ and $\tilde{V}$ is minimized. We motivate the use of the focal frequency loss $\mathcal{L}_{FF}$ by the discrete cosine transform-based compression of the H.264 codec. Since H.264 performs macroblockwise quantization, the focal frequency loss $\mathcal{L}_{FF}$ can be applied on a per-macroblock level. As the file size surrogate loss $\mathcal{L}_{s_f}$, we can use $\mathcal{L}_{S_f} - \alpha_{\rho f}\mathcal{L}_{\rho f} + \alpha_{L1}\mathcal{L}_{L1}$, where $\mathcal{L}_{\rho f}$ is the correlation coefficient loss between the true file size f and the predicted file size $\tilde{f}$. For minimizing the difference between f and $\tilde{f}$ an L1 loss $\mathcal{L}_{L1}$ can be used. Note that the file size can be learned in $\log_{10}$ space, due to the large range of file sizes. $\alpha_{\rho_v}$, $\alpha_{SSIM}$, $\alpha_{FF}$, $\alpha_1$, $\alpha_{\rho_f}$, and $\alpha_{L1}$ denotes the respective positive weight factors, in accordance with aspects of the present invention.

Figure 9:
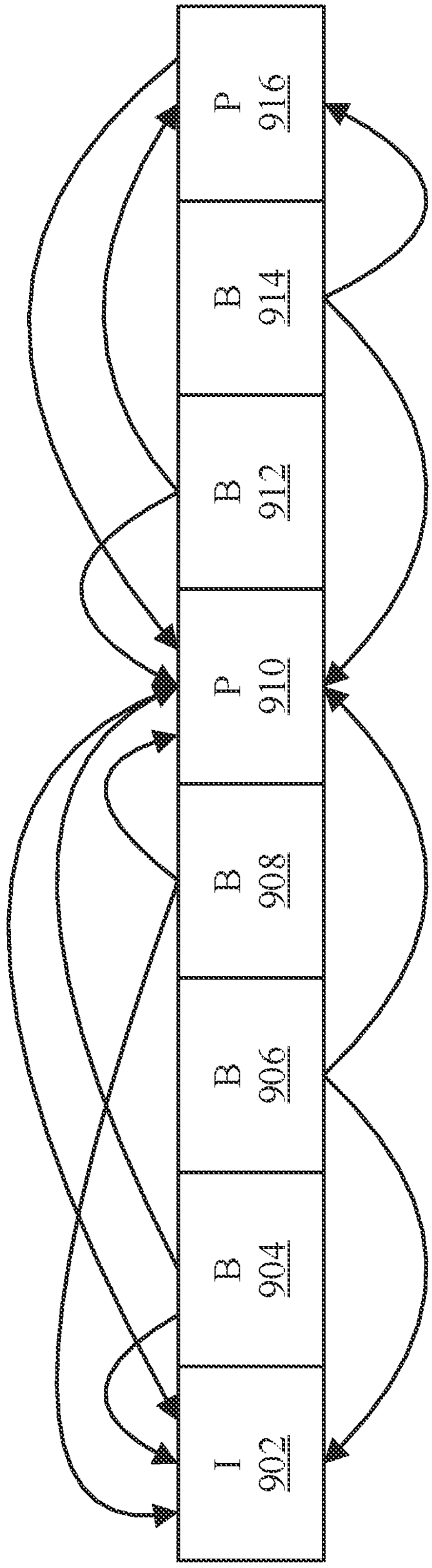
FIG. 9 is a diagram illustratively depicting a high-level view of a Group of Pictures (GOP) structure for an exemplary GOP size of eight (8), in accordance with embodiments of the present invention.

Referring now to FIG. 9, a diagram showing a high-level view of a Group of Pictures (GOP) structure 900 for an exemplary GOP size of eight (8), is illustratively depicted in accordance with embodiments of the present invention.

In various embodiments, the GOP structure 900 is a sequence of frames comprising Intra-coded frames (I-frames) 902, Predicted frames (P-frames) 910 and 916, and Bidirectional frames (B-frames) 904, 906, 908, 912, and 914, which are encoded in a specific order to optimize video compression. In the context of the GOP-ViT, which is inspired by both the H.264 codec and the Vision Transformer (ViT), this structure is leveraged to process video clips efficiently. The GOP-ViT considers the input as a sequence of image tokens with a fixed length corresponding to the GOP. Each image embedding Ti is composed of a number of tokens with an embedding dimension, intended to correspond to the number of macroblocks in each frame.

The diagram shows the closed GOP structure 900 of the H.264 codec for a GOP size of 8, and this structure is particularly advantageous because it allows for a reduction in computational and memory complexity by avoiding the need to construct a large sequence of tokens and instead performing Multi-Head-Attention (MHA) within this closed loop. The MHA is carried out for each frame type, including I, P, and B frames, where the attention mechanism attends to each frame with itself and all corresponding frames based on the GOP structure, as indicated by the curved arrows connecting the frames. For instance, the MHA operation for an I-frame $\hat{T}_{(i,I)}$ can involve the frame attending to itself, while for P and B frames, the operation can involve attending to the current frame as well as the nearest previous and subsequent P-frame or I-frame, as denoted by $T_{(-1,P/I)}$ and $T_{(+1,P/I)}$. This is visually represented by the arrows pointing from each frame to the others it attends to within the GOP structure.

The use of the GOP structure facilitates the efficient processing of video clips, allowing the GOP-ViT to learn both spatial and temporal dependencies within the video sequence. This structure is a critical component of the surrogate model's architecture, as it allows for the approximation of the H.264 function and its derivative, contributing to a low-variance gradient estimator during the training of the surrogate model. The efficiency of this approach is further enhanced by employing standard learnable positional embeddings, extended to the GOP dimension, and by using a frame-wise file size token, which is concatenated to the sequence of image tokens and later used to regress the file size of the encoded video. This innovative method of video processing ensures that the surrogate model can approximate the H.264 function with minimized loss and maximized correlation coefficients, thus achieving an effective balance between video quality and file size, in accordance with aspects of the present invention.

Figure 10:
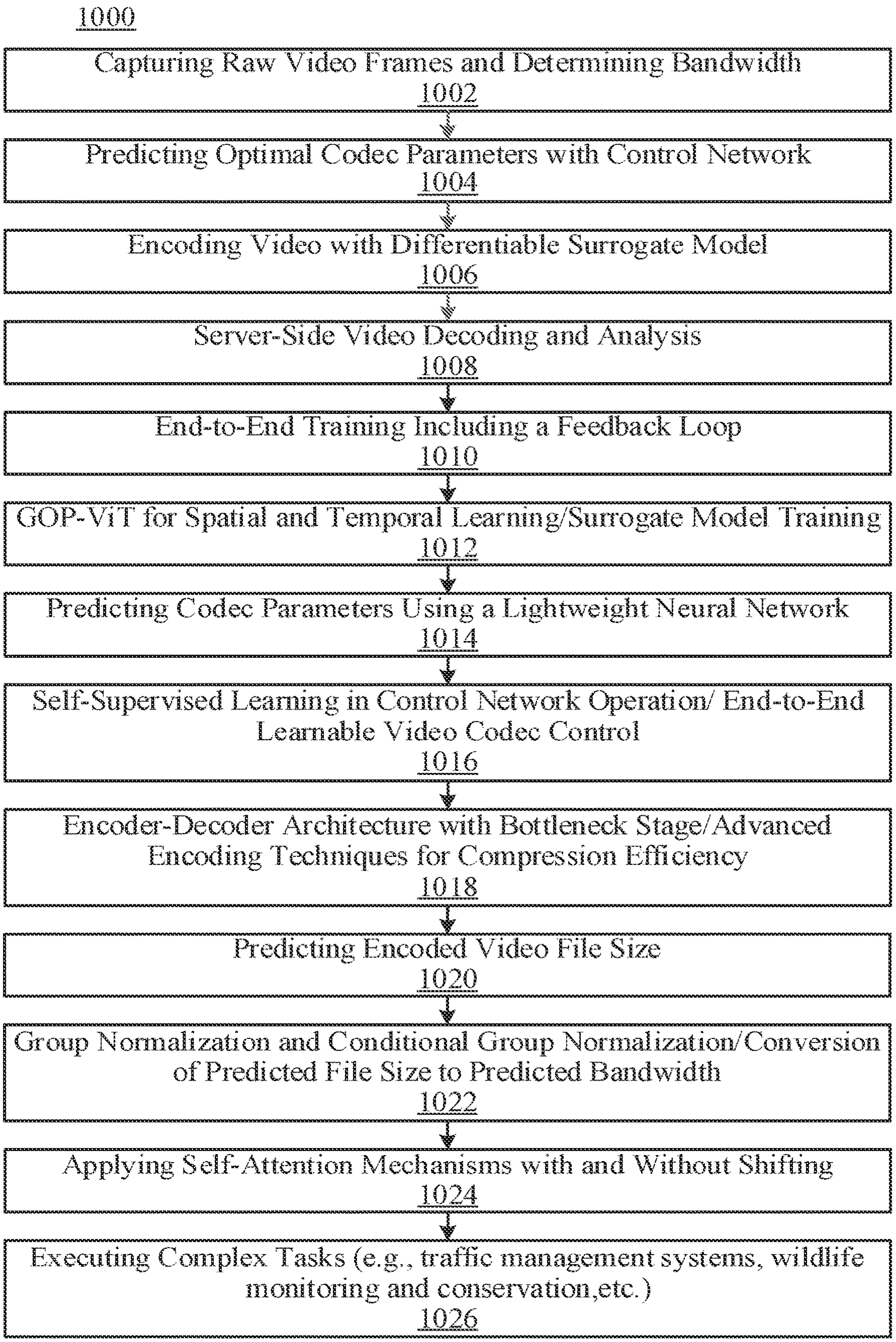
FIG. 10 is a block/flow diagram illustratively depicting a method for optimizing end-to-end video compression control using deep learning models under varying network conditions, in accordance with embodiments of the present invention.

Referring now to FIG. 10, a diagram showing a method 1000 for optimizing end-to-end video compression control using deep learning models under varying network conditions, is illustratively depicted in accordance with embodiments of the present invention.

In various embodiments, in block 1002, raw video frames can be captured on an edge device, which also determines the maximum network bandwidth. This step sets the foundation for adaptive video compression by assessing both the video content and network capacity. Block 1004 involves predicting optimal codec parameters using a control network. The prediction can leverage dynamic network conditions and the content of the video clip, aiming to optimize compression without losing critical data for analysis. A control network predicts optimal codec parameters based on the video content and dynamic network conditions. This prediction is performed in a self-supervised manner, leveraging lightweight neural network architectures to adjust compression settings in real-time, enhancing the balance between compression efficiency and video analysis quality.

In block 1006, the video clip can be encoded using a differentiable surrogate model of a video codec, with the model utilizing the predicted codec parameters. This step allows for the adjustment of codec parameters to ensure video data is optimally prepared for server-side analysis. The video can be encoded using a differentiable surrogate model of the H.264 codec, employing the predicted codec parameters. This model supports macroblock-wise quantization, allowing for fine-grained control over compression to prioritize important video regions for analysis while optimizing bandwidth usage. Block 1008 describes the server decoding the video clip and analyzing it with a deep vision model. The analysis could be for segmentation, object detection, and action recognition, tailored to specific analytical needs. After transmission, the server decodes and analyzes the compressed video with a deep vision model, such as segmentation, object detection, or action recognition models. The process ensures that the compressed video retains sufficient quality for accurate analysis despite the lossy compression.

In some embodiments, in block 1010, analysis from the deep vision model is transmitted back to the control network. This feedback loop mechanism supports an end-to-end training process, enabling continuous refinement of codec parameter prediction based on the analysis outcomes. The feedback loop can enable analysis from the server-side deep vision model and can be used to refine the control network's predictions. This end-to-end training approach allows the system to adaptively improve its compression strategies based on actual analysis performance, leading to a more efficient compression process that preserves essential video features.

In block 1012, GOP-ViT for Spatial and Temporal Learning can be implemented within the surrogate model to efficiently learn both spatial and temporal dependencies within video clips. This approach leverages the structure of groups of pictures (GOP) and the capabilities of Vision Transformers (ViT) to process video sequences effectively. This can include Surrogate Model Training for Approximating H.264 Function, which can accurately and efficiently approximate the H.264 codec's function and its derivatives. The training involves minimizing the difference between the surrogate model's outputs and the actual codec outputs, ensuring high fidelity in the compressed video. In block 1014, implementation of a lightweight neural network architecture within the control network for codec parameter prediction can be executed. The design emphasizes minimal computational overhead while ensuring high accuracy in predicting optimal compression settings that align with current network conditions and video content characteristics. The lightweight nature of the neural network facilitates its deployment on edge devices, enabling real-time video processing without significant delays.

In block 1016, self-supervised learning in Control Network Operation and End-to-End Learnable Video Codec Control can be performed. This step can focus on the control network's ability to operate in a self-supervised learning mode, which leverages unlabeled video data to improve the prediction of codec parameters. This approach reduces the dependency on extensive labeled datasets, making the system more adaptable to various video types and conditions by learning from the intrinsic patterns and correlations within the video data itself. The end-to-end learnable video codec control can include creating an end-to-end learnable system for video codec control by using the differentiable surrogate model and a lightweight control network to dynamically adjust codec parameters in response to changing network conditions and server-side analysis requirements.

In block 1018, the use of an encoder-decoder architecture within the differentiable surrogate model, featuring a bottleneck stage specifically conditioned on macroblock-wise quantization parameters is shown. This configuration can be crucial for effectively balancing the trade-off between compression efficiency and the preservation of video quality essential for analytics. The bottleneck stage plays a key role in distilling and encoding the most relevant information for the subsequent decoding and analytics processes. This can include the use of advanced encoding techniques, including reversible GOP-ViT blocks and 2D residual blocks, to enhance the surrogate model's compression efficiency. These techniques allow for a more nuanced compression that can adapt to the video content's specific characteristics. In block 1020, encoded video file size can be predicted by expanding on the inclusion of a multi-layer perceptron within the surrogate model to accurately predict the file size of the encoded video. This capability is instrumental in managing bandwidth allocation, particularly in constrained network environments, by providing a means to adjust compression settings proactively based on the anticipated file size and available network bandwidth.

In block 1022, group normalization and conditional group normalization can be performed. This block elaborates on the incorporation of group normalization and conditional group normalization layers within the surrogate model. These layers are essential for stabilizing and normalizing the features across the encoded video, enhancing the model's ability to handle variations in video content and compression settings. The conditional aspect allows the normalization process to adapt based on specific encoding parameters, further refining the model's output. This block describes the process of converting the predicted file size into a predicted bandwidth usage, which is then compared with the determined maximum network bandwidth. This step is critical for ensuring that the video compression settings are aligned with network capabilities, preventing potential bottlenecks and ensuring smooth video transmission. This predictive analysis allows for preemptive adjustments to compression settings to avoid exceeding network capacity.

Block 1024 focuses on the nuanced application of self-attention mechanisms, both with and without shifting, in different sub-blocks of the surrogate model. This approach allows for a more versatile adaptation to various video content characteristics, as shifting can alter the focus of attention mechanisms to highlight different aspects of the video data. The combination of both approaches within the model ensures a comprehensive analysis of video content for optimal encoding. In block 1026, complex tasks (e.g., traffic management, wildlife monitoring and conservation, etc.) can be executed by applying aspects of the present invention, demonstrating the control network's versatility and adaptability. This application signifies the method's efficacy in not only traditional video analytics scenarios but also in dynamic and latency-sensitive environments, where maintaining high-quality video streams within strict bandwidth constraints is paramount, in accordance with aspects of the present invention.

Figure 11:
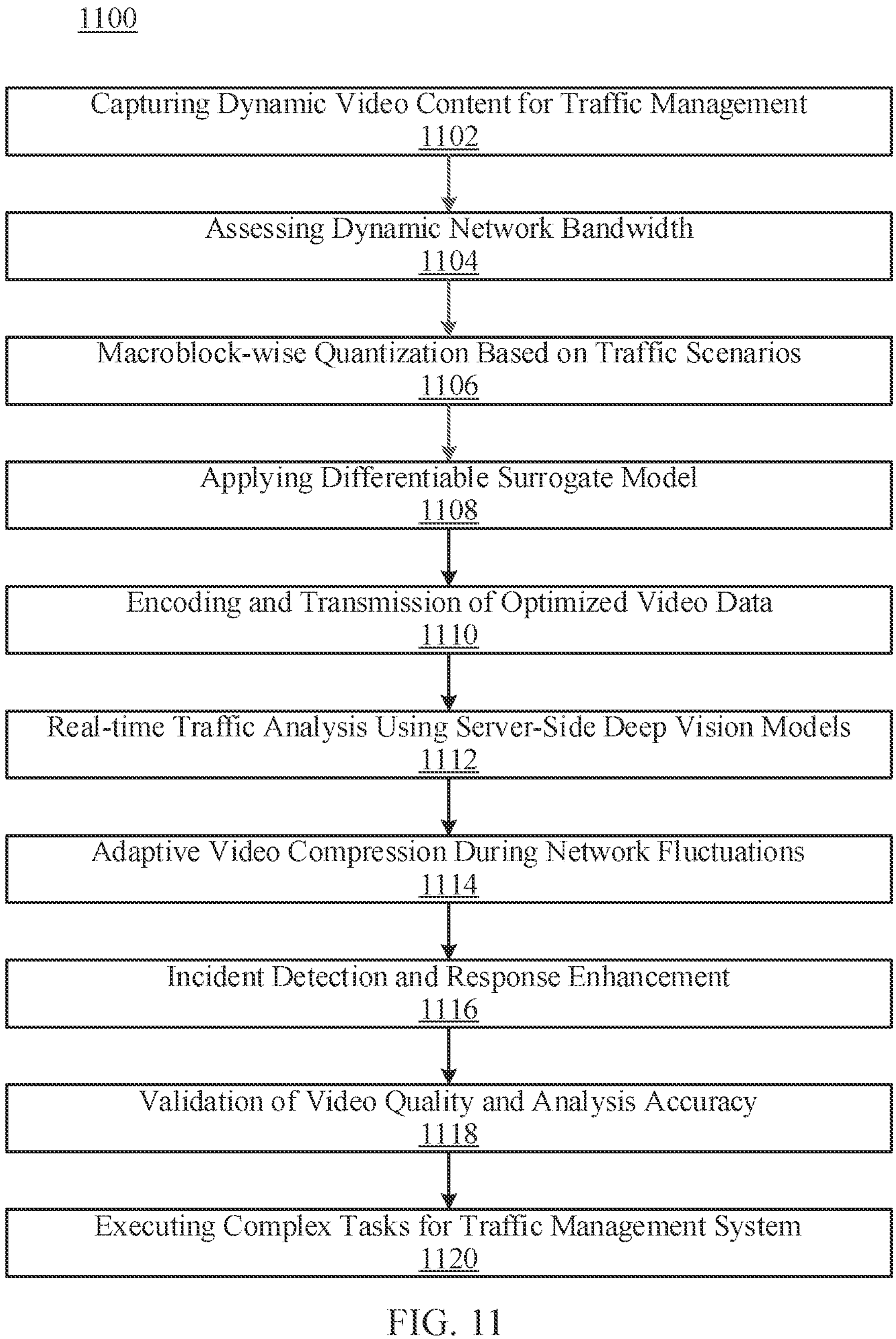
FIG. 11 is a block/flow diagram illustratively depicting a method for optimizing end-to-end video compression control using deep learning models under varying network conditions for traffic management systems, in accordance with embodiments of the present invention.

Referring now to FIG. 11, a block/flow diagram showing a method 1100 for optimizing end-to-end video compression control using deep learning models under varying network conditions for traffic management systems, in accordance with embodiments of the present invention.

This method 1100 demonstrates the real-world utility of an end-to-end learnable control system for H.264 video codec, particularly in the context of traffic management systems. This system significantly enhances the efficiency of video data analysis, crucial for smart city initiatives, especially in monitoring and managing city traffic. In modern smart cities, traffic management systems heavily rely on video data analysis for real-time traffic monitoring, incident detection, and flow optimization. The system can be deployed on edge devices like traffic cameras, which often operate under dynamic network conditions with varying bandwidths. These traffic management systems employ server-side deep vision models for tasks like vehicle detection, pedestrian safety monitoring, and traffic density analysis. Traffic cameras continuously capture high-resolution videos, necessitating efficient compression for transmission to central servers without overloading network bandwidth. The present invention can control the H.264 codec parameters to optimize video compression by dynamically adjusts macroblock-wise quantization parameters based on the current network bandwidth and the content of the video. A novel differentiable surrogate model of the H.264 codec enables the system to adaptively learn and maintain the performance of the server-side deep vision models while optimizing for bandwidth constraints.

In various embodiments, the system and method preserves critical visual details in areas of interest (e.g., road intersections, pedestrian crossings) while compressing less relevant regions. This ensures high-quality data is available for accurate traffic analysis. By intelligently adjusting compression based on network conditions, the system ensures efficient utilization of available bandwidth, crucial for maintaining continuous data flow, especially in high-traffic networks. The system significantly reduces the degradation of deep vision model performance often caused by standard compression techniques, enabling more reliable and accurate traffic management decisions. During peak traffic hours, when network bandwidth might be constrained, the system can adapt by compressing background areas more while retaining higher quality in regions with vehicle and pedestrian activity. In case of incidents, such as traffic accidents, the system ensures that critical regions of the video retain higher quality, aiding in quicker and more accurate responses by traffic management personnel.

In various embodiments, in block 1102, the method begins with the acquisition of video data from traffic cameras. These cameras are strategically placed at various locations, such as intersections and pedestrian crossings, to capture real-time traffic scenarios. The cameras are equipped to handle high-resolution video capture, essential for detailed traffic analysis. Block 1104 involves assessing the current network bandwidth available to each traffic camera. Given that these cameras are often deployed in environments with fluctuating network conditions, it's crucial to constantly evaluate the available bandwidth to optimize video transmission without overloading the network. In block 1106, the method applies macroblock-wise quantization to the video data. This process involves compressing different regions of the video frame (macroblocks) with varying QP values. Regions with high traffic activity or incidents are assigned lower QP values for less compression, maintaining high quality, whereas less critical areas are compressed more (higher QP values).

In block 1108, the method can include application of a differentiable surrogate model of the H.264 codec to the quantized video data. This model, adapted for traffic management scenarios, processes the video to ensure that the compression is aligned with both the network bandwidth constraints and the requirements of server-side deep vision models used for traffic analysis. In block 1110, the method can include encoding and transmitting the processed video data, ensuring it is optimized for transmission over the available network bandwidth. The encoded video retains critical visual details in areas of interest, ensuring that high-quality data is transmitted to central servers for analysis. Block 1112 can involve the use of server-side deep vision models to analyze the transmitted video data. These models can be utilized to perform complex tasks such as vehicle detection, pedestrian safety monitoring, and traffic density analysis. The high-quality video data in critical regions ensures accurate and reliable analysis.

In block 1114, the video compression can be dynamically adapted in response to real-time changes in network bandwidth. During peak traffic hours with constrained bandwidth, the system increases compression in non-essential areas while maintaining quality in critical regions, ensuring continuous and efficient data flow. Block 1116 focuses on incident detection and response. In case of traffic incidents, the system can ensure that regions of interest, such as the location of an accident, are transmitted with higher quality. This facilitates quicker and more accurate responses by traffic management personnel and emergency services. In block 1118, the quality of the transmitted video and the accuracy of the traffic analysis can be validated. This step ensures that the video compression technique does not compromise the efficacy of traffic management strategies, maintaining a high standard of traffic monitoring and incident response. In various embodiments, in block 1120, complex tasks for traffic management systems (e.g., vehicle detection, pedestrian safety monitoring, traffic density analysis, etc.) can be executed in accordance with aspects of the present invention.

Figure 12:
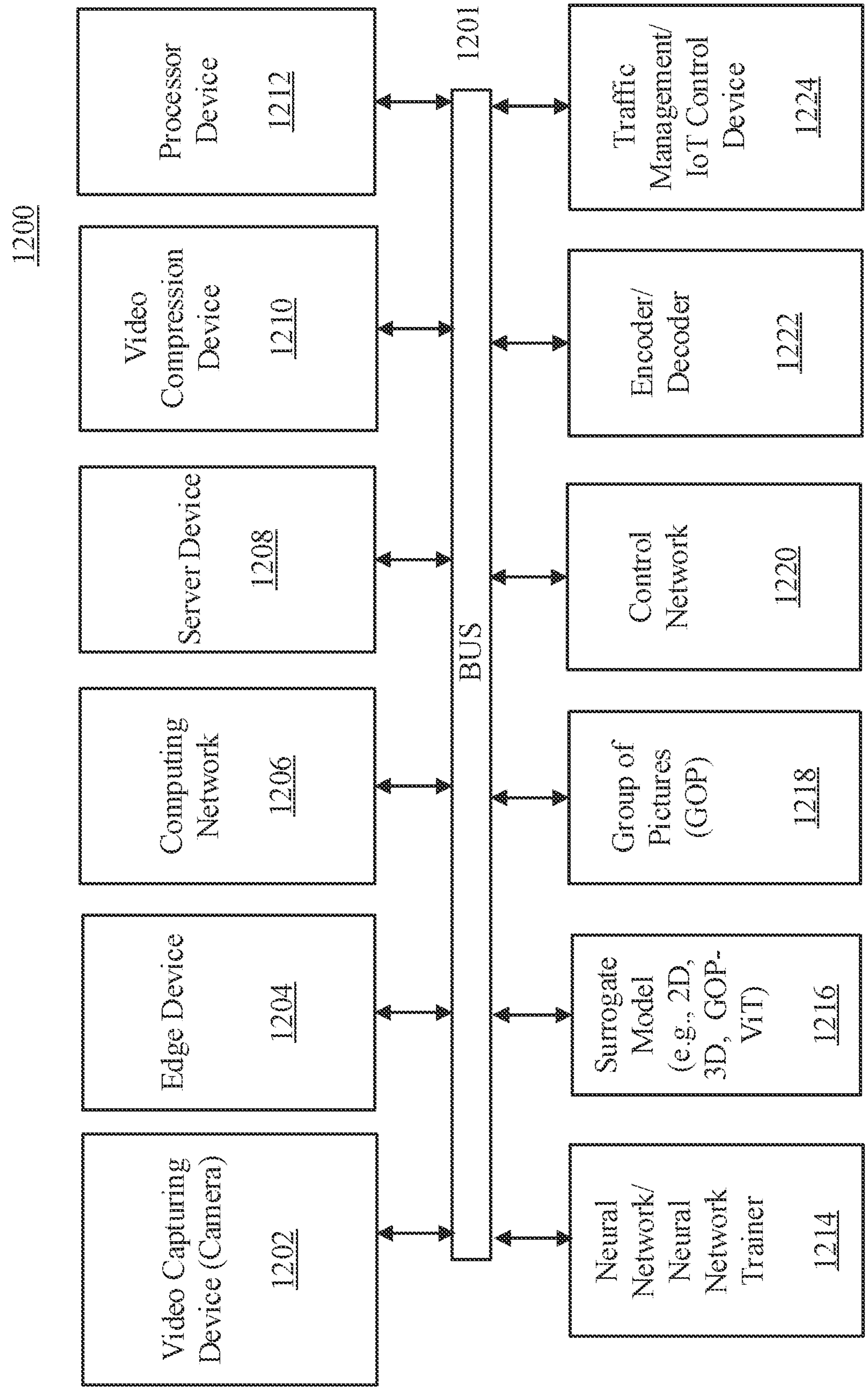
FIG. 12 is a block diagram illustratively depicting a high-level exemplary processing system for optimizing end-to-end video compression control using deep learning models under varying network conditions, in accordance with embodiments of the present invention.

Referring now to FIG. 12, a diagram showing a high-level exemplary processing system 1200 for optimizing end-to-end video compression control using deep learning models under varying network conditions, is illustratively depicted in accordance with embodiments of the present invention.

In various embodiments, a video capturing device (e.g., camera) 1202 can be utilized to capture video content in real-time. The system 1202 can include an edge device 1204, and can transmit data over a computing network 1206 to and from one or more server devices 1208 (e.g., cloud server), and can include one or more processor devices 1212. A video compression device 1210 can compress video, and a neural network/neural network trainer 1214 can be utilized in conjunction with the surrogate model 1216, which can include utilizing a Group of Pictures (GOP) 1218 and a control network 1220, which can further include an encoder and/or decoder 1222, in accordance with aspects of the present invention. A traffic management/IoT control device 1224 can be utilized to monitor areas of interest (e.g., roadway, traffic lights, pedestrian crossings, etc.), and video compression can be adjusted accordingly depending on conditions and needs as identified by the traffic management/IoT control device, in accordance with aspects of the present invention.

Figure 13:
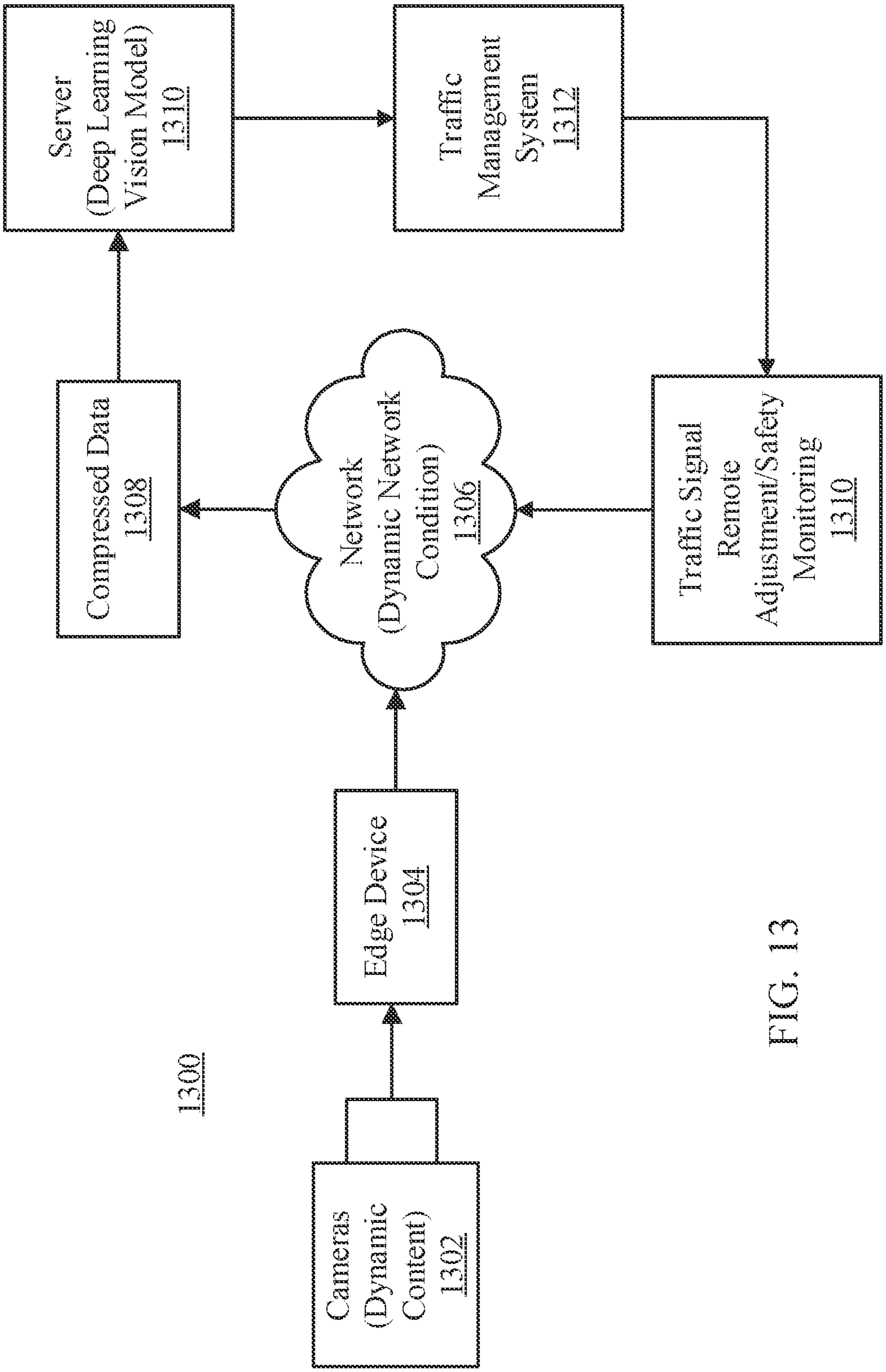
FIG. 13 is a diagram showing a high-level view of a system for traffic management using optimizing end-to-end video compression control and deep learning models under varying network conditions, in accordance with embodiments of the present invention.

Referring now to FIG. 13, a high-level view of a system 1300 for traffic management using optimizing end-to-end video compression control and deep learning models under varying network conditions is illustratively depicted in accordance with embodiments of the present invention.

In an illustrative embodiment, a camera system 1302 can be utilized to monitor an area of interest and/or capture live video and/or image data (e.g., dynamic content). The data can be transmitted to an edge device 1304, which can serve as an initial processing point, including performing preliminary data compression, formatting, analysis, etc. before sending the video and/or image data to the network 1306, which can include dynamic network conditions. In some embodiments, within the network 1306, which represents various dynamic network conditions, the video data may be further compressed, shaped, or prioritized based on current bandwidth and latency metrics to ensure efficient transmission, in accordance with aspects of the present invention. This network 1306 can dynamically adapt the data transmission based on real-time network traffic, bandwidth availability, and various other metrics, potentially altering the data's compression to suit the network conditions. The Compressed Data 1308 represents the video data post network optimization, which is now streamlined for transmission efficiency and ready for analytical processing.

In some embodiments, the data next can be received by the Server (Deep Learning Analytic Unit/Vision Model) 1310, where advanced video analytics can be performed. This server 1310 can utilize deep learning models to analyze the video data for various applications, such as object detection, recognition, and tracking, and to extract meaningful insights from the compressed video data, in accordance with aspects of the present invention. Each block in FIG. 13 represents important steps in the process of capturing, transmitting, and analyzing video data in real-time, ensuring that the dynamic content captured by the camera 1302 is efficiently processed and analyzed despite the constraints and variability of network conditions.

While the single camera system 1302 is shown in FIG. 13 for the sakes of illustration and brevity, it is to be appreciated that multiple camera systems can also be used, in accordance with aspects of the present invention.

In an illustrative embodiment, based on the general video streaming setting shown in FIG. 13, a codec control can be formulated as a constrained planning problem as follows:

$$\max_{(codec\ parameters)} \text{Analytics Model Performance} \quad \text{s.t. Bitrate} \leq \text{Target Bandwidth} \tag{1}$$

For example, a target bandwidth constraint of $10^5$ bits per second can be satisfied by range of codec parameter values (e.g., Quantization Parameter (QP) values from at least 20 to 30) and Equation (1) can select a codec parameter value that results in the maximum possible accuracy of the analytics model, given the target bandwidth constraint. In some embodiments, H. 264 encoding parameters for preserving the performance of a server-side deep vision model while matching a current network-bandwidth requirement can be predicted, and in practice, multiple parameter configurations can satisfy Equation (1).

In some embodiments, given a short video clip and the currently available network bandwidth, the present invention can estimate the codec parameters such that the resulting video stream does not exceed the available network bandwidth. Additionally, when analyzing the encoded/decoded clip with a deep-learning vision model, the performance can be maintained as compared to the performance on the raw clip. Formally, three control requirements to be met by our H. 264 control can be defined: (i) maintain the performance of the server-side deep learning-based vision model, (ii) do not exceed the available bandwidth, preventing information from being dropped by the network, and (iii) perform the codec parameter prediction and encoding in a single forward pass, avoiding complicated feedback loops or multipass encoding, in accordance with aspects of the present invention.

In various embodiments, the present invention can include an end-to-end learnable control of the H. 264 video compression standard for deep learning-based vision models. The present invention can include utilizing a differentiable surrogate model of the non-differentiable H. 264 video codec, which enables differentiating through the video encoding and decoding. In particular, we can propagate gradients from the server-side deep learning vision model through the codec to learn our codec control. Further, a task-agnostic end-to-end training formulation for learning a lightweight edge device side control network to control the H.264 for deep vision models can be implemented utilizing the surrogate model. By utilizing a differentiable surrogate model of the non-differentiable H. 264 codec, we ensure a full differentiability of pipeline. This allows us to utilize end-to-end self-supervised learning, circumventing the use of reinforcement learning, in accordance with aspects of the present invention.

Conventional systems and methods utilize the feedback of a cloud server to decide how a video should be compressed for the server-side deep network. However, a feedback loop leads to a complicated architecture, requires additional bandwidth for the feedback, and adds an additional point of failure, limiting the applicability of such approaches. These approaches also assume that the server-side network runs only a specific task (e.g. object detection). In avoidance of such drawbacks, the present invention can utilize a feedback loop-free and server-side task agnostic codec control pipeline, in accordance with various aspects of the present invention.

In various embodiments, the system 1300 can include a remote traffic management system 1312, which can perform various complex functions related to traffic management responsive to the received data after processing by the server 1310, including, for example, vehicle detection, traffic monitoring, traffic density analysis, etc., in accordance with aspects of the present invention. The traffic management system 1312 can control various traffic-related devices, and can perform remote traffic signal adjustments (e.g., changing color of light, make light blinking, change pedestrian signals remotely, etc.) in block 1310 responsive to instructions from the traffic management system 1312, in accordance with aspects of the present invention.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment. However, it is to be appreciated that features of one or more embodiments can be combined given the teachings of the present invention provided herein.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A system for optimizing video compression using end-to-end learning, comprising:

one or more processor devices operatively coupled to a computer-readable storage medium, the processor devices being configured for:

capturing, using an edge device, raw video frames from a video clip and determining maximum network bandwidth;

predicting, using a control network implemented on the edge device, codec parameters based on network conditions and content of the video clip;

encoding, using a differentiable surrogate model of a video codec, the video clip using the predicted codec parameters and propagating gradients to a server-side vision model to adjust the codec parameters;

transforming spatial data from the video clip into a frequency domain for selective frequency compression for the codec parameters with a Fast Fourier Transform (FFT) block of the differentiable surrogate model to further adjust the codec parameters to balance file size and compression for the video clip;

decoding, using a server, the video clip and analyzing the video clip based on the codec parameters with a server-side deep learning-based vision model;

transmitting, using a feedback mechanism, analysis from the server-side deep learning-based vision model back to the control network to facilitate end-to-end training of the system; and adjusting the encoding parameters based on the analysis from the server-side deep learning-based vision model received from the feedback mechanism.

2. The system of claim 1, wherein the processor is further configured for dynamically assessing, using the control network, network bandwidth availability in real-time and adjusting the predicted codec parameters accordingly to optimize for both video quality and transmission efficiency.

3. The system of claim 1, wherein the differentiable surrogate model of the video codec further comprises a 3D convolutional neural network architecture for accurately modeling behavior of the codec and enabling propagation of gradients for the end-to-end training.

4. The system of claim 1, wherein the encoding further comprises application of a macroblock-wise quantization scheme, directed by the differentiable surrogate model, to selectively adjust compression levels across the video frame based on determined content complexity and importance.

5. The system of claim 1, wherein the feedback mechanism incorporates a loss function specifically designed to measure a discrepancy between original video frames and the decoded video frames as perceived by the server-side deep learning-based vision model, thereby guiding the adjustment of encoding parameters.

6. The system of claim 3, wherein the 3D convolutional neural network architecture of the differentiable surrogate model includes layers configured for feature extraction, quantization parameter prediction, and compression artifact reduction.

7. The system of claim 1, further comprising one or more cameras installed at traffic intersections and pedestrian crossings and configured for capturing and transmitting real-time traffic footage, the processor being configured to adjust video compression in real-time responsive to traffic density and movement patterns detected in the real-time traffic footage.

8. The system of claim 6, wherein the differentiable surrogate model further comprises a multi-layer perceptron (MLP) for a final prediction of quantization parameters (QP), leveraging both spatial and temporal video features extracted by preceding 3D convolutional layers to optimize encoding for subsequent video frames.

9. A method for optimizing video compression using end-to-end learning, comprising:

capturing, using an edge device, raw video frames from a video clip and determining maximum network bandwidth;

predicting, using a control network implemented on the edge device, optimal codec parameters based on dynamic network conditions and content of the video clip;

encoding, using a differentiable surrogate model of a video codec, the video clip using the predicted codec parameters and to propagate gradients to a server-side deep learning-based vision model to adjust the codec parameters;

transforming spatial data from the video clip into a frequency domain for selective frequency compression for the codec parameters with a Fast Fourier Transform (FFT) block of the differentiable surrogate model to further adjust the codec parameters to balance file size and compression for the video clip;

decoding, using a server, the video clip and analyzing the video clip with a deep vision model located on the server;

transmitting, using a feedback mechanism, analysis from the server-side deep learning-based vision model back to the control network to facilitate end-to-end training; and adjusting the encoding parameters based on the analysis from the server-side deep learning-based vision model received from the feedback mechanism.

10. The method of claim 9, further comprising dynamically assessing, using the control network, network bandwidth availability in real-time and adjusting the predicted codec parameters accordingly to optimize for both video quality and transmission efficiency.

11. The method of claim 9, wherein the differentiable surrogate model of the video codec further comprises a 3D convolutional neural network architecture for accurately modeling behavior of the codec and enabling propagation of gradients for the end-to-end training.

12. The method of claim 9, wherein the encoding further comprises application of a macroblock-wise quantization scheme, directed by the differentiable surrogate model, to selectively adjust compression levels across the video frame based on determined content complexity and importance.

13. The method of claim 9, wherein the feedback mechanism incorporates a loss function specifically designed to measure a discrepancy between original video frames and the decoded video frames as perceived by the server-side deep learning-based vision model, thereby guiding the adjustment of encoding parameters.

14. The method of claim 11, wherein the differentiable surrogate model further comprises a multi-layer perceptron (MLP) for a final prediction of quantization parameters (QP), leveraging both spatial and temporal video features extracted by preceding 3D convolutional layers to optimize encoding for subsequent video frames.

15. The system of claim 1, wherein the FFT block includes conditional group normalization (CGN) layers branched in parallel with a real FFT layer stacked with an inverted FFT layer.

* * * * *